(12) United States Patent
Kuwahara et al.

(10) Patent No.: US 12,291,720 B2
(45) Date of Patent: *May 6, 2025

(54) PRODUCTION METHOD FOR RETINAL TISSUE

(71) Applicants: SUMITOMO PHARMA CO., LTD., Osaka (JP); RIKEN, Wako (JP)

(72) Inventors: Atsushi Kuwahara, Kobe (JP); Suguru Yamasaki, Kobe (JP); Yasushi Hiramine, Kobe (JP); Yoshiki Sasai, Wako (JP); Masayo Takahashi, Wako (JP)

(73) Assignees: SUMITOMO PHARMA CO., LTD., Osaka (JP); RIKEN, Wako (JP)

( * ) Notice: Subject to any disclaimer, the term of this patent is extended or adjusted under 35 U.S.C. 154(b) by 674 days.

This patent is subject to a terminal disclaimer.

(21) Appl. No.: 17/567,708

(22) Filed: Jan. 3, 2022

(65) Prior Publication Data

US 2022/0119764 A1    Apr. 21, 2022

Related U.S. Application Data

(63) Continuation of application No. 15/521,387, filed as application No. PCT/JP2015/080017 on Oct. 23, 2015, now Pat. No. 11,214,772.

(30) Foreign Application Priority Data

Oct. 24, 2014  (JP) ................. 2014-217868

(51) Int. Cl.
| | |
|---|---|
| C12N 5/079 | (2010.01) |
| A61K 35/30 | (2015.01) |
| A61K 35/44 | (2015.01) |
| A61L 27/00 | (2006.01) |
| A61L 27/38 | (2006.01) |
| C12N 5/0793 | (2010.01) |
| C12N 5/0797 | (2010.01) |
| C12Q 1/02 | (2006.01) |
| G01N 33/50 | (2006.01) |

(52) U.S. Cl.
CPC ............ *C12N 5/0621* (2013.01); *A61K 35/30* (2013.01); *A61K 35/44* (2013.01); *A61L 27/00* (2013.01); *A61L 27/383* (2013.01); *A61L 27/3895* (2013.01); *C12N 5/0619* (2013.01); *C12N 5/0623* (2013.01); *C12Q 1/02* (2013.01); *G01N 33/5014* (2013.01); *G01N 33/5058* (2013.01); *C12N 2501/115* (2013.01); *C12N 2501/155* (2013.01); *C12N 2501/41* (2013.01); *C12N 2501/50* (2013.01); *C12N 2501/999* (2013.01); *C12N 2506/45* (2013.01); *C12N 2533/52* (2013.01)

(58) Field of Classification Search
CPC .. A61K 35/30; A61L 27/3895; C12N 2501/41
See application file for complete search history.

(56) References Cited

U.S. PATENT DOCUMENTS

| | | |
|---|---|---|
| 8,956,866 B2 | 2/2015 | Idelson et al. |
| 11,214,772 B2 | 1/2022 | Kuwahara et al. |
| 2006/0122111 A1 | 6/2006 | Furukawa |
| 2008/0044901 A1 | 2/2008 | Sasai et al. |
| 2009/0053809 A1 | 2/2009 | Zander et al. |
| 2010/0009442 A1 | 1/2010 | Sasai et al. |
| 2010/0119492 A1 | 5/2010 | Hans et al. |
| 2011/0027333 A1 | 2/2011 | Idelson et al. |
| 2011/0091869 A1 | 4/2011 | Sasai et al. |
| 2011/0223140 A1 | 9/2011 | Park et al. |
| 2011/0274662 A1 | 11/2011 | Malcuit et al. |
| 2012/0129211 A1 | 5/2012 | Kattman et al. |
| 2013/0040330 A1 | 2/2013 | Sasai et al. |
| 2014/0308743 A1 | 10/2014 | Sasai et al. |
| 2014/0341864 A1 | 11/2014 | Nakano et al. |
| 2015/0118749 A1 | 4/2015 | Idelson et al. |
| 2015/0125506 A1 | 5/2015 | Idelson et al. |
| 2015/0132787 A1 | 5/2015 | Sasai et al. |

(Continued)

FOREIGN PATENT DOCUMENTS

| | | |
|---|---|---|
| CN | 101688178 A | 3/2010 |
| EP | 2128244 A1 | 12/2009 |

(Continued)

OTHER PUBLICATIONS

Akopian et al., "Comparison of defined culture systems for feeder cell free propagation of human embryonic stem cells," In Vitro Cell. Dev. Biol. Anim., 46(3-4): 247-258 (2010).

(Continued)

*Primary Examiner* — Taeyoon Kim
*Assistant Examiner* — Nicholas A Humphries
(74) *Attorney, Agent, or Firm* — Leydig, Voit & Mayer, Ltd.

(57) ABSTRACT

The present invention provides a method for producing retinal cells or a retinal tissue, comprising the following steps (1)-(3):

(1) a first step of culturing human pluripotent stem cells in the absence of feeder cells and in a medium comprising a factor for maintaining undifferentiated state, (2) a second step of culturing the pluripotent stem cells obtained in the first step in suspension in the presence of a Sonic hedgehog signal transduction pathway activating substance to form a cell aggregate, and (3) a third step of culturing the aggregate obtained in the second step in suspension in the presence of a 1) a BMP signal transduction pathway activating substance to obtain an aggregate containing retinal cells or a retinal tissue.

18 Claims, 10 Drawing Sheets

(56) References Cited

U.S. PATENT DOCUMENTS

| | | |
|---|---|---|
| 2016/0186134 A1 | 6/2016 | Keller et al. |
| 2016/0186136 A1 | 6/2016 | Sasai et al. |
| 2016/0244721 A1 | 8/2016 | Sawada et al. |
| 2016/0251616 A1 | 9/2016 | Nakano et al. |
| 2016/0264936 A1 | 9/2016 | Nakano et al. |
| 2016/0376554 A1 | 12/2016 | Kuwahara et al. |
| 2017/0253853 A1 | 9/2017 | Sasai et al. |
| 2017/0313976 A1 | 11/2017 | Kuwahara et al. |
| 2017/0313981 A1 | 11/2017 | Kuwahara et al. |
| 2017/0319748 A1 | 11/2017 | Kuwahara et al. |
| 2018/0245039 A1 | 8/2018 | Ando et al. |
| 2018/0258388 A1 | 9/2018 | Ando et al. |
| 2019/0127670 A1 | 5/2019 | Kuwahara et al. |

FOREIGN PATENT DOCUMENTS

| | | |
|---|---|---|
| JP | 2012-507285 A | 3/2012 |
| JP | 2012-070731 A | 4/2012 |
| JP | 2012-245007 A | 12/2012 |
| JP | 2013-099345 A | 5/2013 |
| WO | WO 2006/053629 A1 | 5/2006 |
| WO | WO 2009/148170 A1 | 12/2009 |
| WO | WO 2011/043591 A2 | 4/2011 |
| WO | WO 2011/055855 A1 | 5/2011 |
| WO | WO 2012/135621 A2 | 10/2012 |
| WO | WO 2013/065763 A1 | 5/2013 |
| WO | WO 2013/077425 A1 | 5/2013 |
| WO | WO 2015/025967 A1 | 2/2015 |
| WO | WO 2015/053375 A1 | 4/2015 |
| WO | WO 2015/054526 A2 | 4/2015 |
| WO | WO 2015/068505 A1 | 5/2015 |
| WO | WO 2015/107738 A1 | 7/2015 |
| WO | WO 2016/032263 A1 | 3/2016 |
| WO | WO 2016/039317 A1 | 3/2016 |
| WO | WO 2016/063985 A1 | 4/2016 |
| WO | WO 2016/063986 A1 | 4/2016 |
| WO | WO 2017/043604 A1 | 3/2017 |
| WO | WO 2017/043605 A1 | 3/2017 |

OTHER PUBLICATIONS

Amoroso et al., "Accelerated High-Yield Generation of Limb-Innervating Motor Neurons from Human Stem Cells," *J. Neurosci.*, 33(2): 574-586 (2013).

Boucherie et al., "Brief Report: Self-Organizing Neuroepithelium from Human Pluripotent Stem Cells Facilitates Derivation of Photoreceptors," *Stem Cells*, 31(2):408-414 (2013).

Chambers et al., "Highly efficient neural conversion of human ES and iPS cells by dual inhibition of SMAD signaling," *Nat. Biotechnol.*, 27(3): 275-280 (2009).

Chen, "Chemically defined conditions for human iPSC derivation and culture," *Nat. Methods*, 8(5): 424-429 (2011).

Davis-Dusenbery et al., "How to make spinal motor neurons," *Development*, 141(3): 491-201 (2014).

Denayer et al., "Canonical Wnt Signaling Controls Proliferation of Retinal Stem/Progenitor Cells in Postembryonic Xenopus Eyes," *Stem Cells*, 26(28): 2063-2074 (2008).

Doi et al., "Isolation of Human Induced Pluripotent Stem Cell-Derived Dopaminergic Progenitors by Cell Sorting for Successful Transplantation," *Stem Cell Reports*, 2(3): 337-350 (2014).

Du et al., "Regulation of Retinal Progenitor Cell Differentiation by Bone Morphogenetic Protein 4 is Mediated by the Smad/Id Cascade," *Invest. Ophthalmol. Vis. Sci.*, 51(7): 3764-3773 (2010).

Eiraku, "Self-Organized Formation of Polarized Cortical Tissues from ESCs and Its Active Manipulation by Extrinsic Signals," *Cell Stem Cell*, 3(5): 519-532 (2008).

Eiraku et al., "Relaxation-expansion model for self-driven retinal morphogenesis," *Bioessays*, 34(1): 17-25 (2011).

Eiraku et al., "Self-organizing optic-cup morphogenesis in three-dimensional culture," *Nature*, 472(7341): 51-56 (2011).

Faravelli et al., "Motor neuron derivation from human embryonic and induced pluripotent stem cells: experimental approaches and clinical perspectives," *Stem Cell Res. Ther.*, 5(4): 87 (2014).

Fuhrmann, "Wnt signaling in eye organogenesis," *Organogenesis*, 4(2): 60-67 (2008).

Furuta et al., "BMP4 is essential for lens induction in the mouse embryo," *Genes Dev.*, 12(23): 3764-3775 (1998).

Hu et al., "Neural differentiation of human induced pluripotent stem cells follows developmental principles but with variable potency," *Proc. Natl. Acad. Sci. U.S.A.*, 107(9): 4335-4340 (2010).

Ikeda et al., "In vitro neuronal differentiation induction using ES cells—telencephalic precursors and neural retinal precursors,"*Experimental Medicine*, 24(2): 188-194 (2006).

Kadoshima et al., "Self-organization of axial polarity, inside-out layer pattern, and species-specific progenitor dynamics in human ES cell-derived neocortex," *Proc. Natl. Acad. Sci. U.S.A.*, 110(50): 20284-20289 (2013).

Kubo et al., "Wnt2b controls retinal cell differentiation at the ciliary marginal zone," *Development*, 130(3): 587-598 (2003).

Kubo et al., "Hairy1 acts as a node downstream of Wnt signaling to maintain retinal stem cell-like progenitor cells in the chick ciliary marginal zone," *Development*, 136(11): 1823-1833 (2009).

Kuwahara et al., "Generation of a ciliary margin-like stem cell niche from self- organizing human retinal tissue," *Nat. Commun.*, 6: 6286 (2015).

Lamba et al., "Efficient generation of retinal progenitor cells from human embryonic stem cells," *Pro Natl., Acad. Sci. U.S.A.*, 103(34): 12769-12774 (2006).

Lancaster et al., "Cerebral organoids model human brain development and microcephaly," *Nature*, 501 (7467): 373-379 (2013).

Lang, "Pathways regulating lens induction in the mouse," *Int. J. Dev. Biol.*, 48(8-9): 783-791 (2004).

La Torre et al., "Production and Transplantation of Retinal Cells from Human and Mouse Embryonic Stem Cells," *Retinal Development: Methods and Protocols, Methods in Molecular Biology*, 884: 229-246 (2012).

Loebel et al., "Lineage choice and differentiation in mouse embryos and embryonic stem cells," *Dev. Biol.*, 264(1): 1-14 (2003).

Messina et al., "Noggin-Mediated Retinal Induction Reveals a Novel Interplay Between Bone Morphogenetic Protein Inhibition, Transforming Growth Factor β, and Sonic Hedgehog Signaling," *Stem Cells*, 33(8): 2496-2508 (2015).

Miyazawa et al., "Two major Smad pathways in TGF-beta superfamily signaling," *Genes to Cell*, 7(12): 1191-1204 (2002).

Morizane et al., "Neural Induction with a Dopaminergic Phenotype from Human Pluripotent Stem Cells Through a Feeder-Free Floating Aggregation Culture," *Methods Mol. Biol.*, 1018: 11-19 (2013).

Muguruma et al., "Ontogeny-recapitulating generation and tissue integration of ES cell-derived Purkinje cells," *Nat. Neurosci.*, 13(10): 1171-1180 (2010).

Nakagawa et al., "A novel efficient feeder-free culture system for the derivation of human induced pluripotent stem cells," *Sci. Rep.*, 4: 3594 (2014).

Nakano et al., "Self-Formation of Optic Cups and Storable Stratified Neural Retina from Human ESCs," *Cell Stem Cell*, 10(6): 771-785 (2012).

Osakada et al., "Control of neural differentiation from pluripotent stem cells," *Inflammation and Regeneration*, 28(3): 166-173 (2008).

Osakada et al., "Toward the generation of rod and con photoreceptors from mouse, monkey and human embryonic stem cells," *Nat. Biotechnol.*, 26(2): 215-224 (2008).

Osakada et al., "In vitro differentiation of retinal cells from human pluripotent stem cells by small-molecule induction," *J. Cell Sci.*, 122(17): 3169-3179 (2009).

Osakada et al., "Neural Induction and Patterning in Mammalian Pluripotent Stem Cells," *CNS & Neurological Disorders—Drug Targets*, 10(4): 419-432 (2011).

Ozair, "Neural induction and early patterning in vertebrates," *WIREs Dev. Biol.*, 2(4): 479-498 (2013).

Sasai, "Self-organization as seen in pattern formation of neural tissue: Challenge to Emergent Biology," *Brain Science Review*, 99-112 (2014).

(56) References Cited

OTHER PUBLICATIONS

Seiler et al., "Visual restoration and transplant connectivity in degenerate rats implanted with retinal progenitor sheets," *Eur. J. Neurosci.*, 31: 508-520 (2010).
Stanton et al., "Small-molecule modulators of the *Sonic Hedgehog* signaling pathway," *Mol. Biosyst.*, 6(1): 44-54 (2010).
Stephens et al., "Loss of *adenomatous polyposis coli* (*apc*) Results in an Expanded Ciliary Marginal Zone in the Zebrafish Eye," *Dev. Dyn.*, 239(7): 2066-2077 (2010).
Suga et al., "Self-formation of functional adenohypophysis in three-dimensional culture," *Nature*, 480(7375): 57-62 (2011).
Trousse et al., "BMP4 Mediates Apoptotic Cell Death in the Developing Chick Eye," *J. Neurosci.*, 21(4): 1292-1301 (2001).
Vugler et al., "Embryonic stem cells and retinal repair," *Mech. Dev.*, 124(11-12): 807-829 (2007).
Watanabe et al., "Directed differentiation of telencephalic precursors from embryonic stem cells," *Nat. Neurosci.*, 8(3): 288-296 (2005).
Wei et al., "Isolation and identification of retinal stem cells in mouse eye," *Journal of Third Military Medical University*, 25(24): 2161-2164 (2003).
Yang et al., "Directed Differentiation into Neural Lineages and Therapeutic Potential of Porcine Embryonic Stem Cells in Rat Parkinson's Disease Model," *Cell Reprogram.*, 12(4): 447-461 (2010).
Yang et al., "Efficient generation of lens progenitor cells and lentoid bodies from human embryonic stem cells in chemically defined conditions," *FASEB J.*, 24(9): 3274-3283 (2017).
Zhang et al., "Rapid and Efficient Generation of Neurons from Human Pluripotent Stem Cells in a Multititre Plate Format," *J. Vis. Exp.*, 73: e4335 (2013).
Zhou et al., "Differentiation of human embryonic stem cells into cone photoreceptors through simultaneous inhibition of BMP, TGFβ and Wnt signaling," *Development*, 142(19): 3294-3306 (2015).
European Patent Office, Supplementary European Search Report in European Patent Application No. 15852025 (Apr. 20, 2018).
European Patent Office, Communication Pursuant to Rule 164(1) EPC in European Patent Application No. 15852504.8 (May 14, 2018).
European Patent Office, Extended European Search Report in European Patent Application No. 15852504.8 (Sep. 6, 2018).
European Patent Office, Extended European Search Report in European Patent Application No. 17786064.0 (Oct. 17, 2019).
European Patent Office, Extended European Search Report in European Patent Application No. 21166628.4 (Jul. 19, 2021).
Japanese Patent Office, International Search Report in International Patent Application No. PCT/JP2017/016120 (Jul. 11, 2017).

PRODUCTION METHOD FOR RETINAL TISSUE

TECHNICAL FIELD

The present invention relates to a method for producing retinal cells or a retinal tissue from pluripotent stem cells.

BACKGROUND ART

As a method for producing a neural tissue such as retinal tissue from pluripotent stem cells, a method for producing neural tissue which comprises forming uniformed aggregates of pluripotent stem cells in a serum-free medium, culturing them in suspension, culturing them in suspension in a culture medium for differentiation induction in the presence of a differentiation-inducing factor and the like as appropriate to induce differentiation of pluripotent stem cells into the intended neural cells has been reported (patent document 1 and non-patent document 1). For example, a method for obtaining a multi-layered retinal tissue from pluripotent stem cells (non-patent document 2 and patent document 2), and a method for obtaining multi-layered retinal tissue which comprises forming uniformed aggregates of pluripotent stem cells in a serum-free medium containing a Wnt signal transduction pathway inhibiting substance, followed by culturing them in suspension in the presence of a basement membrane preparation, and then culturing them in suspension in a serum-containing medium (non-patent document 3 and patent document 3) are known. In addition, a method for inducing differentiation of pluripotent stem cells into a hypothalamic tissue (patent document 4 and non-patent document 4), and a method inducing differentiation of pluripotent stem cells into neural precursor cells (non-patent document 5 and 6) have also been reported.

The pluripotent stem cells as a starting material of these production methods, particularly in the case of primate pluripotent stem cells, were cultured to maintain undifferentiated state in the presence of feeder cells and with the addition of a factor for maintaining undifferentiated state. In recent years, improvement has been made in the culturing to maintain undifferentiated state, and a method of culturing primate pluripotent stem cells in the absence of feeder cells (feeder-free) with the addition of a factor for maintaining undifferentiated state has been reported (non-patent document 7, non-patent document 8 and non-patent document 9). A stable method for producing retinal cells or a retinal tissue, which uses pluripotent stem cells subjected to feeder-free culturing by this method as a starting material has been desired.

DOCUMENT LIST

Patent Documents

[patent document 1] WO 2009/148170
[patent document 2] WO 2011/055855
[patent document 3] WO 2013/077425
[patent document 4] WO 2013/065763

Non-Patent Documents

[non-patent document 1] Cell Stem Cell, 3, 519-32 (2008)
[non-patent document 2] Nature, 472, 51-56 (2011)
[non-patent document 3] Cell Stem Cell, 10(6), 771-775 (2012)
[non-patent document 4] Nature, 480, 57-62 (2011)
[non-patent document 5] Nature Biotechnology, 27(3), 275-80 (2009)
[non-patent document 6] Proc Natl Acad Sci USA, 110 (50), 20284-9 (2013)
[non-patent document 7] Nature Methods, 8, 424-429 (2011)
[non-patent document 8] Scientific Reports, 4, 3594 (2014)
[non-patent document 9] In Vitro Cell Dev Biol Anim., 46, 247-58 (2010)

SUMMARY OF THE INVENTION

Problems to be Solved by the Invention

The problem to be solved by the present invention is provision of a method for producing retinal cells or retinal tissues from pluripotent stem cells prepared or cultured to maintain undifferentiated state in the absence of feeder cells.

Means of Solving the Problems

The present inventors have conducted intensive studies in an attempt to solve the aforementioned problems and found that a spherical cell aggregate having a smooth surface and a dense inside, and maintaining an undifferentiated state can be formed with high efficiency by culturing pluripotent stem cells (particularly human iPS cells) while maintaining undifferentiated state in the absence of feeder cells, and subjecting the obtained pluripotent stem cells to suspension culturing in a medium containing a Sonic hedgehog signal transduction pathway activating substance to form a cell aggregate. In addition, the present inventors have found that by using this high quality cell aggregate, retinal cells or retinal tissues can be induced with high efficiency, which resulted in the completion of the present invention.

That is, the present invention relates to the following.

[1] A method for producing retinal cells or a retinal tissue, comprising the following steps (1)-(3):
(1) a first step of culturing human pluripotent stem cells in the absence of feeder cells and in a medium comprising a factor for maintaining undifferentiated state,
(2) a second step of culturing the pluripotent stem cells obtained in the first step in suspension in the presence of a Sonic hedgehog signal transduction pathway activating substance to form a cell aggregate, and
(3) a third step of culturing the aggregate obtained in the second step in suspension in the presence of a BMP signal transduction pathway activating substance to obtain an aggregate containing retinal cells or a retinal tissue.

[2] The production method of [1], wherein, in the second step, the cells obtained in the first step are dispersed, and the dispersed cells are cultured in suspension.

[3] The production method of [1] or [2], wherein the factor for maintaining undifferentiated state is an FGF signal transduction pathway activating substance.

[4] The production method of [3], wherein the FGF signal transduction pathway activating substance is bFGF.

[5] The production method of any of [1]-[4], wherein, in the second step, the concentration of the Sonic hedgehog signal transduction pathway activating substance in the medium is a concentration corresponding to Sonic hedgehog signal transduction activity of SAG at 10 nM to 700 nM.

[6] The production method of any of [1]-[5], wherein the Sonic hedgehog signal transduction pathway activating substance is SAG, Purmorphamine or Shh.

[7] The production method of any of [1]-[6], wherein the BMP signal transduction pathway activating substance is one or more proteins selected from the group consisting of BMP2, BMP4, BMP7 and GDF7.

[8] The production method of [6], wherein the BMP signal transduction pathway activating substance is BMP4.

[9] The production method of any of [1]-[8], wherein, in the third step, the BMP signal transduction pathway activating substance is added to the medium between day 2 and day 9 after the start of the second step.

[10] The production method of any of [1]-[9], wherein, in the third step, the aggregate is cultured in a medium containing a Sonic hedgehog signal transduction pathway activating substance at a concentration not more than a concentration corresponding to Sonic hedgehog signal transduction activity of SAG at 700 nM.

[11] The production method of any of [1]-[10], wherein the first step is performed by an adhesion culturing method.

[12] The production method of any of [1]-[11], wherein the pluripotent stem cells are induced pluripotent stem cells.

[13] The production method of any of [1]-[12], wherein uniformed aggregates are formed in the second step.

[14] The production method of any of [1]-[13], wherein the aggregate obtained in the third step comprises one or more cells selected from the group consisting of retinal progenitor cell, neural retinal progenitor cell, photoreceptor precursor cell, photoreceptor cell, rod photoreceptor cell, cone photoreceptor cell, horizontal cell, amacrine cell, interneuron, ganglion cell, retinal pigment epithelial cell, and ciliary marginal zone cell.

[15] The production method of any of [1]-[14], wherein the suspension culturing is performed in the absence of a basement membrane preparation.

[16] A reagent for evaluating toxicity or efficacy of a test substance, comprising retinal cells or a retinal tissue produced by the method of any of [1]-[15].

[17] A method for evaluating toxicity or efficacy of a test substance, comprising bringing the substance into contact with retinal cells or a retinal tissue produced by the method of any of [1]-[15], and detecting an influence of the substance on the cells or tissue.

[18] A medicament for treating a disease due to a disorder of a retinal tissue, comprising retinal cells or a retinal tissue produced by the method of any of [1]-[15].

[19] The medicament of [18], wherein the retinal cells are retinal progenitor cells and/or retinal layer-specific neurons.

[20] A method for treating a disease due to a disorder of a retinal tissue, comprising transplanting an effective amount of retinal cells or a retinal tissue produced by the method of any of [1]-[15] to a subject in need of the transplantation.

[21] Retinal cells or a retinal tissue produced by the method of any of [1]-[15] for use in the treatment of a disease due to a disorder of a retinal tissue.

[22] A pharmaceutical composition comprising retinal cells or a retinal tissue produced by the method of any of [1]-[15] as an active ingredient.

Effect of the Invention

According to the present invention, a high quality cell aggregate, as well as retinal cells and retinal tissues can be produced with high efficiency from pluripotent stem cells cultured in the absence of feeder cells.

DESCRIPTION OF EMBODIMENTS

1. Definition

Figure 1:
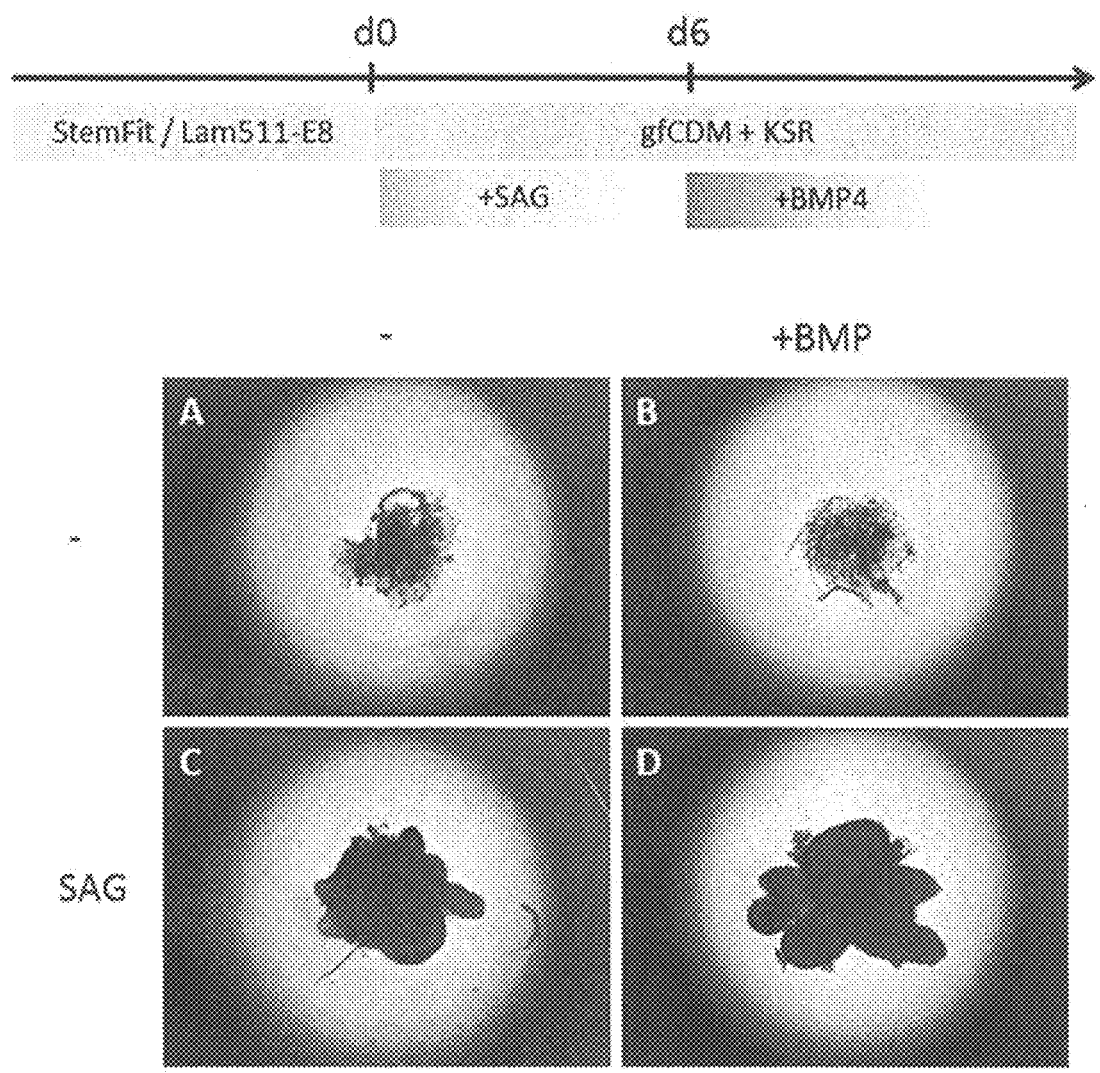
FIG. 1 shows culture conditions of Comparative Example 1 and Example 1, and bright field images of aggregates (A-D).

In the present invention, "stem cell" means an undifferentiated cell having differentiation potency and proliferative capacity (particularly self-renewal competence) maintaining differentiation potency. The stem cell includes subpopulations such as pluripotent stem cell, multipotent stem cell, unipotent stem cell and the like according to the differentiation potency. Pluripotent stem cell refers to a stem cell capable of being cultured in vitro and having a potency to differentiate into any cell lineage belonging to three germ layers (ectoderm, mesoderm, endoderm) and/or tissue derived from extraembryonic tissue (pluripotency). The multipotent stem cell means a stem cell having a potency to differentiate into plural types of tissues or cells, though not all kinds. The unipotent stem cell means a stem cell having a potency to differentiate into a particular tissue or cell.

Pluripotent stem cell can be induced from fertilized egg, clone embryo, germ stem cell, stem cell in a tissue, somatic cell and the like. Examples of the pluripotent stem cell include embryonic stem cell (ES cell), EG cell (embryonic germ cell), induced pluripotent stem cell (iPS cell) and the like. Muse cell (Multi-lineage differentiating stress enduring cell) obtained from mesenchymal stem cell (MSC), and GS cell produced from reproductive cell (e.g., testis) are also encompassed in the pluripotent stem cell. Embryonic stem cell was first established in 1981, and has also been applied to the generation of knockout mouse since 1989. In 1998, human embryonic stem cell was established, which is also being utilized for regenerative medicine. ES cell can be produced by culturing an inner cell mass on a feeder cell or in a medium containing LIF. The production methods of ES cell are described in, for example, WO 96/22362, WO 02/101057, U.S. Pat. Nos. 5,843,780, 6,200,806, 6,280,718 and the like. Embryonic stem cells are available from given organizations, or a commercially available product can be purchased. For example, human embryonic stem cells, KhES-1, KhES-2 and KhES-3, are available from Kyoto University's Institute for Frontier Medical Sciences. EB5 cell, which is a mouse embryonic stem cell, is available from Incorporated Administrative Agency RIKEN, and D3 cell line, which is a mouse embryonic stem cell, is available from ATCC.

Nuclear transfer ES cell (ntES cell), which is one of the ES cells, can be established from a clone embryo produced by transplanting the nucleus of a somatic cell into an enucleated egg.

EG cell can be produced by culturing a primordial germ cell in a medium containing mSCF, LIF and bFGF (Cell, 70: 841-847, 1992).

The "induced pluripotent stem cell" in the present invention is a cell induced to have pluripotency by reprogramming a somatic cell by a known method and the like. Specifically, a cell induced to have pluripotency by reprogramming differentiated somatic cells such as fibroblast, peripheral blood mononuclear cell and the like by the expression of a combination of a plurality of genes selected from the group consisting of reprogramming genes including Oct3/4, Sox2, Klf4, Myc (c-Myc, N-Myc, L-Myc), Glis1, Nanog, Sall4, lin28, Esrrb and the like can be mentioned. Examples of preferable combination of reprogramming factors include (1) Oct3/4, Sox2, Klf4, and Myc (c-Myc or L-Myc), and (2) Oct3/4, Sox2, Klf4, Lin28 and L-Myc (Stem Cells, 2013; 31:458-466).

Induced pluripotent stem cell was established by Yamanaka et al. in mouse cell in 2006 (Cell, 2006, 126(4), pp. 663-676). In 2007, Induced pluripotent stem cell was also established from human fibroblast, and has pluripotency and self-renewal competence similar to those of embryonic stem cells (Cell, 2007, 131(5), pp. 861-872; Science, 2007, 318(5858), pp. 1917-1920; Nat. Biotechnol., 2008, 26(1), pp. 101-106). Besides the production method based on direct reprogramming by gene expression, induced pluripotent stem cell can also be obtained from somatic cell by the addition of a compound and the like (Science, 2013, 341, pp. 651-654).

It is also possible to obtain established induced pluripotent stem cell and, for example, human induced pluripotent cell lines established by Kyoto University such as 201B7 cell, 201B7-Ff cell, 253G1 cell, 253G4 cell, 1201C1 cell, 1205D1 cell, 1210B2 cell or, 1231A3 cell and the like are available from Kyoto University and iPS Academia Japan, Inc. As the established induced pluripotent stem cell, for example, Ff-I01 cell and Ff-I14 cell established by Kyoto University are available from Kyoto University.

While the somatic cell used for obtaining induced pluripotent stem cell is not particularly limited, tissue-derived fibroblast, blood-lineage cells (e.g., peripheral blood mononuclear cell, T cell), hepatocyte, pancreatic cell, intestinal epithelial cell, smooth muscle cell and the like can be mentioned.

When induced pluripotent stem cell is produced by reprogramming by the expression of several kinds of genes, the means for gene expression is not particularly limited. Examples of the aforementioned means include an infection method using a virus vector (e.g., retrovirus vector, lentivirus vector, Sendaivirus vector, adenovirus vector, adeno-associated virus vector), a gene transfer method using a plasmid vector (e.g., plasmid vector, episomal vector) (e.g., calcium phosphate method, lipofection method, RetroNectin method, electroporation method), a gene transfer method using an RNA vector (e.g., calcium phosphate method, lipofection method, electroporation method), a method with direct injection of protein and the like.

An induced pluripotent stem cell can be produced in the presence of a feeder cell or in the absence of feeder cells (feeder-free). When produced in the presence of a feeder cell, the induced pluripotent stem cell can be produced by a known method in the presence of a factor for maintaining undifferentiated state. While a medium to be used for producing an induced pluripotent stem cell in the absence of feeder cells is not particularly limited, a known maintenance medium for embryonic stem cells and/or induced pluripotent stem cells, and a medium for establishing induced pluripotent stem cell under feeder-free can be used. Examples of the medium for establishing an induced pluripotent stem cell under feeder-free conditions include feeder-free media such as Essential 8 medium, TeSR medium, mTeSR medium, mTeSR-E8 medium, StemFit medium and the like. For example, an induced pluripotent stem cell can be produced by gene transfer of 4 factors of Oct3/4, Sox2, Klf4, and Myc into somatic cell by using a Sendaivirus vector in the absence of feeder cells.

The pluripotent stem cell to be used in the present invention is preferably ES cell or induced pluripotent stem cell, more preferably induced pluripotent stem cell.

As the multipotent stem cell, tissue stem cells (also called stem cell in tissue, tissue-specific stem cell or somatic stem cell) such as hematopoietic stem cell, neural stem cell, retinal stem cell, mesenchymal stem cell and the like can be mentioned.

Genetically-modified pluripotent stem cells can be produced by using, for example, a homologous recombination technique. Examples of the gene on the chromosome to be modified include a cell marker gene, a histocompatibility antigen gene, a gene related to a disease due to a disorder of neural cell and so on. A target gene on the chromosome can be modified using the methods described in Manipulating the Mouse Embryo, A Laboratory Manual, Second Edition, Cold Spring Harbor Laboratory Press (1994); Gene Targeting, A Practical Approach, IRL Press at Oxford University Press (1993); Biomanual Series 8, Gene Targeting, Making of Mutant Mouse using ES cell, YODOSHA CO., LTD. (1995); and so on.

To be specific, for example, the genomic DNA comprising the target gene to be modified (e.g., cell marker gene, histocompatibility antigen gene, disease-related gene and so on) is isolated, and a targetting vector used for homologous recombination of the target gene is produced using the isolated genomic DNA. The produced targetting vector is introduced into stem cells and the cells that showed homologous recombination between the target gene and the targetting vector are selected, whereby stem cells having the modified gene on the chromosome can be produced.

Examples of the method for isolating genomic DNA comprising the target gene include known methods described in Molecular Cloning, A Laboratory Manual, Second Edition, Cold Spring Harbor Laboratory Press (1989), Current Protocols in Molecular Biology, John Wiley & Sons (1987-1997) and so on. The genomic gene comprising the target gene can also be isolated using genomic DNA library screening system (manufactured by Genome Systems), Universal GenomeWalker Kits (manufactured by CLONTECH) and so on. A polynucleotide encoding the target protein can also be used instead of genome DNA. The polynucleotide can be obtained by amplifying the corresponding polynucleotide by the PCR method.

Production of targetting vector used for homologous recombination of the target gene, and efficient selection of a homologous recombinant can be performed according to the methods described in Gene Targeting, A Practical Approach, IRL Press at Oxford University Press (1993); Biomanual Series 8, Gene Targeting, Making of Mutant Mouse using ES cell, YODOSHA CO., LTD. (1995); and so on. As the targetting vector, any of replacement type or insertion type can be used. As the selection method, methods such as positive selection, promoter selection, negative selection, polyA selection and so on can be used.

Examples of a method for selecting the desired homologous recombinant from the selected cell lines include Southern hybridization method, PCR method and so on for the genomic DNA.

The "mammal" in the present invention encompasses rodents, ungulata, carnivora, primates and the like. The rodents encompass mouse, rat, hamster, guinea pig and the like. Ungulata encompass swine, bovine, goat, horse, sheep and the like. Carnivora encompasses dog, cat and the like. The "primates" in the present invention refers to mammals belonging to the primate, and the primates include prosimian such as lemur, loris, tupai and the like, and anthropoidea such as monkey, ape, human and the like.

The pluripotent stem cell to be used in the present invention is a human pluripotent stem cell, more preferably a human induced pluripotent stem cell (iPS cell) or human embryonic stem cell (ES cell).

The "suspension culturing" or "suspension culture method" in the present invention refers to culturing while maintaining a state in which cells or cell aggregates are suspended in a culture medium and a method of performing the culture. That is, suspension culturing is performed under conditions in which cells or cell aggregates are not adhered to a culture vessel and the like, and culturing performed under conditions permitting adhesion to a culture vessel and the like (adhesion culturing or adhesion culture method) is not included in the category of suspension culturing. In this case, adhesion of cell means that a strong cell-substratum junction is formed between a cell or cell aggregate and a culture vessel. More particularly, suspension culturing refers to culturing under conditions in which a strong cell-substratum junction is not formed between a cell or cell aggregate and a culture vessel, and adhesion culturing refers to culturing under conditions in which a strong cell-substratum junction is formed between a cell or cell aggregate and a culture vessel and the like.

In a cell aggregate in suspension culture, a planar cell-cell adhesion is formed. In cell aggregates in suspension culture, a cell-substratum junction is hardly formed with a culture vessel and the like and, even if it is formed, its contribution is small. In some embodiment, an endogenous cell-substratum junction is present inside the aggregate, but a cell-substratum junction is hardly formed with a culture vessel and the like and, even if it is formed, its contribution is small.

The planar cell-cell adhesion (plane attachment) means that a cell attaches to another cell via planes. More particularly, the planar cell-cell adhesion means that, for example, not less than 1%, preferably not less than 3%, more preferably not less than 5%, of the surface area of a cell adheres to the surface of another cell. A surface of a cell can be observed by staining with a reagent (e.g., DiI) that stains membranes, immunostaining of cell adhesion molecules (e.g., E-cadherin and N-cadherin).

The cell culture vessel to be used when performing suspension culturing is not particularly limited as long as it enables "culturing in suspension" and those of ordinary skill in the art can appropriately determine same. Examples of such cell culture vessel include flask, tissue culture flask, culture dish (dish), petri dish, tissue culture dish, multidish, microplate, microwell plate, micropore, multiplate, multi-well plate, chamber slide, schale, tube, tray, culture bag, Erlenmeyer flask, spinner flask, roller bottle and so on. To enable suspension culturing, these culture vessels are preferably non-cell-adherent. Useful non-cell-adherent culture vessels include culture vessels whose surfaces have not undergone an artificial treatment for improving the cell adhesiveness (e.g., surface treatment with extracellular matrix such as basement membrane preparation, laminin, entactin, collagen, gelatin etc., and the like, or coating treatment with polymer such as polylysine, polyornithine and the like or positive electric charge treatment and the like), and the like. As a non-cell-adherent culture vessel, culture vessels whose surfaces have been artificially treated to decrease adhesiveness to the cells (e.g., superhydrophilic treatment with MPC polymer and the like, protein low adsorption treatment etc.) and the like can be used. Roller culture using spinner flask, roller bottle and the like may be performed. The culture surface of the culture vessel may be a flat bottom or may have concaves and convexes.

A culture vessel used for adhesion culturing is not particularly limited as long as "adhesion culturing" can be performed, and those of ordinary skill in the art can appropriately select a culture vessel suitable according to the culture scale, culture conditions and period for the culturing. Examples of such culture vessel include flasks, tissue culture flasks, culture dishes (dishes), tissue culture dishes, multidishes, microplates, micro-well plates, multi-plates, multi-well plates, chamber slides, schale, tubes, trays, culture bags, microcarrier, bead, stack plate, spinner flask and roller bottles. To enable adhesion culturing, these culture vessels are preferably cell-adherent. Cell-adherent culture vessels include culture vessels whose surfaces have been artificially treated to improve cell adhesiveness, and specifically, a surface-processed culture vessel, or, a culture vessel whose inside is coated with a coating agent can be mentioned. Examples of the coating agent include extracellular matrix such as laminin [including laminin $\alpha 5\beta 1\gamma 1$ (hereinafter laminin 511), laminin $\alpha 1\beta 1\gamma 1$ (hereinafter laminin 111) and the like and laminin fragment (laminin 511E8 etc.)], entactin, collagen, gelatin, vitronectin, Synthemax (Corning Incorporated), Matrigel and the like, or polymers such as polylysine, polyornithine and the like. Examples of the surface-processed culture vessel include culture vessels surface-processed by a positive electric charge treatment and the like.

The medium to be used for culturing cells in the present invention can be prepared from a medium generally used for culturing animal cells as a basal medium. Examples of the basal medium include media that can be used for culturing animal cells such as BME medium, BGJb medium, CMRL1066 medium, Glasgow MEM (GMEM) medium, Improved MEM Zinc Option medium, IMDM medium, Medium199 medium, Eagle MEM medium, αMEM medium, DMEM medium, F-12 medium, DMEM/F-12 medium, IMDM/F12 medium, Ham medium, RPMI1640 medium, Fischer's medium, and mixed medium thereof etc.

The "serum-free medium" in the present invention means a medium free of unadjusted or unpurified serum. In the present invention, a medium containing purified blood-derived components and animal tissue-derived components (e.g., growth factor) is also included in a serum-free medium unless unadjusted or unpurified serum is contained therein.

The serum-free medium may contain a serum alternative. Examples of the serum alternative include one appropriately containing albumin, transferrin, fatty acid, collagen precursor, trace element, 2-mercaptoethanol or 3' thiolglycerol, or equivalents of these etc., and so on. Such serum alternative may be prepared by, for example, the method described in WO98/30679. In addition, the serum alternative may be a commercially available product. Examples of such commercially available serum alternative include Knockout™ Serum Replacement (Life Technologies, now ThermoFisher: hereinafter sometimes to be indicated as KSR), Chemically Defined Lipid Concentrated (manufactured by Life Technologies) and Glutamax™ (manufactured by Life Technologies), B27 (manufactured by Life Technologies), N2 supplement (manufactured by Life Technologies).

The serum-free medium to be used for suspension culturing may appropriately contain a fatty acid or lipid, amino acid (e.g., non-essential amino acids), vitamin, growth factor, cytokine, antioxidant, 2-mercaptoethanol, pyruvic acid, buffering agent, inorganic salts and so on.

To avoid complicated preparation, a serum-free medium supplemented with an appropriate amount (e.g., about 0.5% to about 30%, preferably about 1% to about 20%) of commercially available KSR (manufactured by Life Technologies) may be used as such serum-free medium (e.g., medium of 1:1 mixture of F-12 medium and IMDM medium supplemented with 10% KSR, 1× Chemically-defined Lipid concentrated (CDLC), and 450 µM 1-monothioglycerol). As a product equivalent to KSR, the medium disclosed in JP-A-2001-508302 can be mentioned.

The "serum-containing medium" in the present invention means a medium containing unadjusted or unpurified serum. The medium may contain a fatty acid, lipid, amino acid (e.g., non-essential amino acids), vitamin, growth factor, cytokine, antioxidant, 2-mercaptoethanol, 1-monothioglycerol, pyruvic acid, buffering agent, inorganic salts and so on. For example, a serum medium can be used in the step of maintaining the neural tissue (e.g., retinal tissue) produced by the present invention (to be also referred to as mature culture).

In the present invention, the culturing is preferably performed under xeno-free conditions. The "xeno-free" means conditions eliminating components derived from species different from that of the cell to be cultured.

In the present invention, the "medium containing substance X" and "in the presence of substance X" refer to a medium supplemented with an exogenous substance X or a medium containing an exogenous substance X, or in the presence of an exogenous substance X. That is, when the cells or tissues present in the medium endogenously express, secrete or produce substance X, the endogenous substance X is distinguished from the exogenous substance X, and a medium free of exogenous substance X is understood to fall outside the category of the "medium containing substance X", even when it contains endogenous substance X.

For example, a "medium containing a Sonic hedgehog signal transduction pathway activating substance" is a medium supplemented with an exogenous Sonic hedgehog signal transduction pathway activating substance or a medium containing an exogenous Sonic hedgehog signal transduction pathway activating substance.

In the present invention, a feeder cell refers to a cell other than a stem cell co-exist when culturing the stem cell. Examples of the feeder cells used for culturing pluripotent stem cells while maintaining undifferentiated state include mouse fibroblasts (MEF etc.), human fibroblasts, SNL cells and the like. As the feeder cells, feeder cells that underwent a growth suppression treatment is preferable. Examples of the growth suppression treatment include treatment with a growth inhibitor (e.g., mitomycin C), gamma radiation, UV irradiation and the like. Feeder cells used for culturing pluripotent stem cells while maintaining undifferentiated state contributes to the maintenance of undifferentiation of pluripotent stem cell by secretion of a humoral factor (preferably factor for maintaining undifferentiated state), or production of a scaffold for cell adhesion (extracellular substrate).

In the present invention, the absence of feeder cells (feeder-free) means culturing in the absence of feeder cells. The absence of feeder cells means, for example, conditions free of addition of feeder cells, or conditions substantially free of feeder cells (e.g., the ratio of the number of feeder cells relative to the total number of cells is not more than 3%).

In the present invention, an "aggregate" of cells refers to a clump formed by assembly of cells dispersed in a medium, wherein the cells are adhered to each other. Cell clumps, embryoid bodies, spheres, spheroids are also encompassed in the cell aggregates. Preferably, a planar cell-cell adhesion is formed in the aggregate of cells. In some embodiments, cells sometimes form a cell-cell junction and/or a cell adhesion, for example, adherence junction, in some or all of the aggregates. The "aggregate" in the present invention specifically includes an aggregate produced in the second step of the above-mentioned present invention [1], which is formed by cells dispersed at the time of the start of the suspension culturing, and an aggregate produced in the third step of the above-mentioned present invention [1], which contains induced retinal cells differentiated from pluripotent stem cell, and the "aggregate" also includes an aggregate already formed at the time of the start of the second step in the above-mentioned present invention [1] (i.e., at the time of the start of suspension culture). The cell aggregate formed in the second step encompasses "embryoid body (EB)".

In the present invention, "uniformed aggregates" means that the size of each aggregate is constant when a plurality of aggregates are cultured, and that the variance in the length of the maximum diameter is small when the size of the aggregates are evaluated by the length of the maximum diameter. More specifically, it means that not less than 75% of aggregates in the whole aggregate population are within mean ±100%, preferably mean ±50%, more preferably mean ±20%, of the maximum diameter in the population of the aggregates.

In the present invention, to "form uniformed cell aggregates" means to "rapidly aggregate a given number of dispersed cells" to form cell aggregates uniform in size, when gathering the cells to form cell aggregates and culturing the aggregates in suspension.

Dispersion refers to dividing cells or a tissue into small cell clots (not less than 2 cells and not more than 100 cells, preferably not more than 50 cells) or single cells by a dispersion treatment such as enzymatic treatment, physical treatment and the like. A given number of dispersed cells is a collection of a certain number of cell clots or single cells.

Examples of the method of dispersing pluripotent stem cells include a mechanical dispersion treatment, a cell dispersion solution treatment, and a cell protecting agent addition treatment. These treatments may be performed in combination. Preferably, a cell dispersion treatment is performed and then a mechanical dispersion treatment is performed.

As a method of mechanical dispersion treatment, a pipetting treatment or scraping operation by a scraper can be mentioned.

As a cell dispersion solution to be used for the cell dispersion solution treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

When pluripotent stem cells are dispersed, cell death of the pluripotent stem cells may be suppressed by treating with a cell protecting agent. As a cell protecting agent to be used for the cell protecting agent treatment, a FGF signal transduction pathway activating substance, heparin, an IGF signal transduction pathway activating substance, serum, and serum alternative can be mentioned. To suppress cell death induced by dispersion (particularly, cell death of human pluripotent stem cells), a Rho-associated coiled-coil kinase (ROCK) inhibiting substance or a Myosin inhibiting substance may be added at the time of dispersion. As a ROCK inhibiting substance, Y-27632, Fasudil (HA1077), H-1152 and the like can be mentioned. As a Myosin inhibiting substance, Blebbistatin can be mentioned. As a preferable cell protecting agent, a ROCK inhibiting substance can be mentioned.

For example, a method for dispersing pluripotent stem cells includes, for example, a method involving treating a colony of pluripotent stem cells with a cell dispersion solution (TrypLE Select) in the presence of a ROCK inhibiting substance as a cell protecting agent, and further dispersing them by pipetting.

In the production method of the present invention, it is preferable to form an aggregate of pluripotent stem cells by rapidly gathering the pluripotent stem cells. When an aggregate of pluripotent stem cells is formed in such a manner, an epithelium-like structure can be formed with good reproducibility in the cells induced and differentiated from the formed aggregate. Examples of the experimental operation to form an aggregate include a method involving keeping cells in a small space by using a plate with small wells (e.g., plate with wells having a base area of about 0.1-2.0 $cm^2$ when calculated in terms of flat bottom), micropore and so on, a method involving aggregating cells by centrifugation for a short time using a small centrifugation tube. As a plate with small wells, for example, 24 well plate (area of about 1.88 $cm^2$ when calculated in terms of flat bottom), 48 well plate (area of about 1.0 $cm^2$ when calculated in terms of flat bottom), 96 well plate (area of about 0.35 $cm^2$ when calculated in terms of flat bottom, inner diameter about 6-8 mm), and 384 well plate can be mentioned. Preferred is 96 well plate. As a shape of the plate with small wells, the shape of the bottom surface when the well is seen from above is, for example, polygon, rectangle, ellipse, true circle, preferably true circle. As a shape of the plate with small wells when the well is seen from the side well, the shape of the bottom surface may be a flat bottom structure or a structure having high outer circumference and low inner concave. The shape of the bottom surface includes, for example, U-bottom, V-bottom, M-bottom, preferably U-bottom or V-bottom, more preferably V-bottom. As a plate with small wells, a cell culture dish (e.g., 60 mm-150 mm dish, culture flask) with a concave convex, or dent on the bottom surface may also be used. The bottom surface of a plate with small wells is preferably a non-cell-adhesive bottom surface, preferably the aforementioned non-cell-adhesive-coated bottom surface.

Formation of aggregates of pluripotent stem cells or aggregates of a cell population containing pluripotent stem cells, and uniformity thereof can be determined based on the size of the aggregate mass and the number of cells therein, macroscopic morphology, microscopic morphology by tissue staining analysis and homogeneity thereof, and the like. In addition, formation of an epithelial-like structure in the aggregate, and uniformity thereof can be determined based on the macroscopic morphology of the aggregate, microscopic morphology by tissue staining analysis and uniformity thereof, expression of differentiation and undifferentiation markers and uniformity thereof, control of expression of differentiation marker and synchronism thereof, reproducibility of differentiation efficiency between aggregates, and so on.

The "tissue" in the present invention refers to a structure of a cell population having a structure in which one kind of cells having a uniformed morphology or property, or plural types of cells having different morphologies and properties are sterically arranged in a given pattern.

In the present invention, the "neural tissue" refers to a tissue constituted of neural cells including cerebrum, midbrain, cerebellum, spinal cord, retina, peripheral nerve, forebrain, hindbrain, telencephalon, diencephalon and the like in the developing stage or adult stage. A neural tissue sometimes forms an epithelial structure (neuroepithelium) having a layer structure, and the amount of neuroepithelium in cell aggregates can be evaluated by bright field observation using an optical microscope.

In the present invention, the "neural cell" refers to a cell other than epidermal lineage cell in a tissue derived from ectoderm. That is, it includes cells such as neural precursor cell, neuron (neuronal cell), glia, neural stem cell, neuron precursor cell, glial precursor cell and the like. The neural cell also encompasses cell constituting the below-mentioned retinal tissue (retinal cell), retinal progenitor cell, retinal layer-specific neuron, neural retinal cell, and retinal pigment epithelial cell. The neural cell can be identified by using Nestin, TuJ1, PSA-NCAM, N-cadherin and the like as a marker.

Neuron (or neuronal cell) is a functional cell that forms a neural circuit and contributes to signal transduction, and can be identified by using the expression of immature neuronal markers such as TuJ1, Dcx, HuC/D and the like and/or mature neuronal cell markers such as Map2, NeuN and the like as an index.

As glia, astrocyte, oligodendrocyte, Müller glia and the like can be mentioned. As an astrocyte marker, GFAP can be mentioned; as an oligodendrocyte marker, O4 can be mentioned, and as a Müller glia marker, CRALBP and the like can be mentioned.

The neural stem cell is a cell having differentiation potency (multipotency) into neuron and glial cell, and proliferative capacity (sometimes to be referred to as self-renewal competence) maintaining multipotency. As the neural stem cell marker, Nestin, Sox2, Musashi, Hes family, CD133 and the like can be mentioned; however, these markers are markers for progenitor/precursor cells in general and are not considered neural stem cell-specific markers. The number of neural stem cells can be evaluated by neurosphere assay, clonal assay and the like.

The neuronal precursor cell is a cell having proliferative capacity, which produces neuron and does not produce glial cell. As a neuronal precursor cell marker, Tbr2, Tα1 and the like can be mentioned. Alternatively, an immature neuronal marker (TuJ1, Dcx, HuC/D)-positive and growth marker (Ki67, pH3, MCM)-positive cell can also be identified as a neuronal precursor cell.

The glial precursor cell is a cell having proliferative capacity, which produces glial cell and does not produce neuron.

The neural precursor cell is an assembly of precursor cells including neural stem cell, neuronal precursor cell and glial precursor cell, and has proliferative capacity and neuron- and glia-productivity. The neural precursor cell can be identified using Nestin, GLAST, Sox2, Sox1, Musashi, Pax6 and the like as markers. Alternatively, a neural cell marker-positive and growth marker (Ki67, pH3, MCM)-positive cell can also be identified as a neural precursor cell.

In the present invention, the "retinal tissue" means a tissue in which one type or at least two or more types of cells such as photoreceptor cells, photoreceptor precursor cells, rod photoreceptor cells, cone photoreceptor cells, interneurons, horizontal cells, bipolar cells, amacrin cells, retinal ganglion cells (ganglion cells), retinal pigment epithelial cell (RPE), ciliary marginal zone cell, their progenitor/precursor cells, and retinal progenitor cells and so on, which constitute respective retinal layers in retina in vivo, are sterically arranged in layers. The retinal layer which is constituted by each cell can be confirmed by a known method, for example, presence or absence of the expression of a cell marker or the level thereof, etc.

The "retinal layer" in the present invention means each layer constituting the retina. Specific examples thereof include retinal pigment epithelial layer, photoreceptor layer, external limiting membrane, outer nuclear layer, outer plexiform layer, inner nuclear layer, inner plexiform layer, ganglion cell layer, nerve fiber layer and inner limiting membrane.

The "retinal progenitor cell" in the present invention refers to a progenitor cell capable of differentiating into any mature retinal cell including photoreceptor cell, horizontal cell, bipolar cell, amacrine cell, retinal ganglion cell, retinal pigment epithelial cell and the like.

In the present invention, the "neural retinal progenitor cell" refers to a progenitor cell capable of differentiating into any one of or plural mature retinal cells including photoreceptor cell, horizontal cell, bipolar cell, amacrine cell, retinal ganglion cells, and the like. In general, a neural retinal progenitor cell does not differentiate into a retinal pigment epithelial cell.

The photoreceptor precursor cell, horizontal cell precursor cell, bipolar cell precursor cell, amacrine cell precursor cell, retinal ganglion cell precursor cell, and retinal pigment epithelial precursor cell refer to precursor cells committed to differentiate into photoreceptor cell, horizontal cell, bipolar cell, amacrine cell, retinal ganglion cells, and retinal pigment epithelial cell, respectively.

In the present invention, the "retinal layer-specific neuron" is a cell constituting a retina layer and is a neuronal cell (neuron) specific to the retinal layer. Examples of the retinal layer-specific neuron include bipolar cell, retinal ganglion cells, amacrine cell, horizontal cell, photoreceptor cell, retinal pigment epithelial cell, rod cell and cone cell.

The "retinal cell" in the present invention encompasses the aforementioned retinal progenitor cells and retinal layer specific neurons.

Examples of the retinal cell marker include Rx (also referred to as Rax), PAX6 and Chx10 expressed in retinal progenitor cell, Nkx2.1 expressed in precursor cell of hypothalamus neuron but not expressed in retinal progenitor cell, Sox1 expressed in hypothalamus neuroepithelium but not expressed in retina, Crx, Blimp1 and the like expressed in precursor cell of photoreceptor cell, and the like. Examples of the marker of the retinal layer-specific neuron include Chx10, PKCα and L7 expressed in bipolar cell, TUJI and Brn3 expressed in retinal ganglion cells, Calretinin expressed in amacrine cell, Calbindin expressed in horizontal cell, Rhodopsin and Recoverin expressed in mature photoreceptor cell, Nrl and Rhodopsin expressed in rod cell, Rxr-gamma and S-Opsin expressed in cone cell, RPE65 and Mitf expressed in retinal pigment epithelium cell, Rdh10 and SSEA1 expressed in ciliary marginal zone and the like.

2. Method for Producing Retinal Cells or a Retinal Tissue

The production method of the present invention is a method for producing retinal cells or a retinal tissue, comprising the following steps (1)-(3):

(1) a first step of culturing human pluripotent stem cells in the absence of feeder cells and in a medium comprising a factor for maintaining undifferentiated state, (2) a second step of culturing the pluripotent stem cells obtained in the first step in suspension in the presence of a Sonic hedgehog signal transduction pathway activating substance to form a cell aggregate, and (3) a third step of culturing the aggregate obtained in the second step in suspension in the presence or absence of a differentiation-inducing factor to obtain an aggregate containing retinal cells or a retinal tissue.

In step (1), human pluripotent stem cells are cultured in the absence of feeder cells and in a medium containing a factor for maintaining undifferentiated state.

As a human pluripotent stem cell in step (1), human induced pluripotent stem cell or human embryonic stem cell (ES cell) can be mentioned.

The production method of induced pluripotent stem cells is not particularly limited, and it can be produced by a method well known to those of ordinary skill in the art as mentioned above. It is also desirable to perform a step for preparing induced pluripotent stem cells (that is, a step of reprogramming somatic cells to establish pluripotent stem cells) under feeder-free condition.

While the production method of embryonic stem cells (ES cells) is not particularly limited, and can be produced by a method well known to those of ordinary skill in the art as mentioned above, it is also desirable to perform a step for preparing embryonic stem cells (ES cells) under feeder-free condition.

The maintenance culturing or expansion culturing for obtaining pluripotent stem cells to be used in step (1) can be performed by a method well known to those of ordinary skill in the art as mentioned above. While the above-mentioned maintenance culturing and expansion culturing of pluripotent stem cells can be performed by adhesion culturing or suspension culturing, it is preferably performed by adhesion culturing. While the above-mentioned step of maintenance culturing and expansion culturing of pluripotent stem cells may be performed in the presence of feeders or under feeder-free condition, it is preferably performed under feeder-free condition.

The absence of feeder cells (feeder-free) in step (1) means a condition substantially free of feeder cells (e.g., the ratio of the number of feeder cells relative to the total number of cells is not more than 3%). Preferably, step (1) is performed under a condition free of feeder cells.

The medium to be used in step (1) is not particularly limited as long as it is a medium enabling culturing of pluripotent stem cells to maintain undifferentiated state under feeder-free conditions (feeder-free medium). Preferably, to enable culturing to maintain undifferentiated state, it contains a factor for maintaining undifferentiated state. For example, it is a medium containing a factor for maintaining undifferentiated state, and free of a TGFβ family signal transduction pathway inhibiting substance and a Sonic hedgehog signal transduction pathway activating substance.

The factor for maintaining undifferentiated state is not particularly limited as long as it is a substance having an action to suppress differentiation of pluripotent stem cells. Examples of the factor for maintaining undifferentiated state widely used by those of ordinary skill in the art include a FGF signal transduction pathway activating substance, a TGFβ family signal transduction pathway activating substance, insulin and the like in the case of primed pluripotent stem cells (e.g., human ES cells, human iPS cells). As the FGF signal transduction pathway activating substance, fibroblast growth factors (e.g., bFGF, FGF4, FGF8) can be specifically mentioned. As the TGFβ family signal transduction pathway activating substance, a TGFβ signal transduction pathway activating substance, a Nodal/Activin signal transduction pathway activating substance can be mentioned. As the TGFβ signal transduction pathway activating substance, TGFβ1, TGFβ2 can be mentioned. As the Nodal/Activin signal transduction pathway activating substance, Nodal, Activin A, Activin B can be mentioned. When human pluripotent stem cells (human ES cells, human iPS cells) are cultured, the medium in step (1) preferably contains bFGF as a factor for maintaining undifferentiated state.

The factor for maintaining undifferentiated state to be is used in the present invention is generally a factor for maintaining undifferentiated state of mammals. The mammals are, for example, those mentioned above. Since the factor for maintaining undifferentiated state may have cross-reactivity among mammal species, a factor for maintaining undifferentiated state of any mammal may also be used as long as the undifferentiated state of the pluripotent stem cells to be cultured can be maintained. Preferably, a factor for maintaining undifferentiated state of a mammal of the same species as the cells to be cultured is used. For example, for the culturing of human pluripotent stem cells, human factor for maintaining undifferentiated states (e.g., bFGF, FGF4, FGF8, EGF, Nodal, Activin A, Activin B, TGFβ 1, TGFβ 2 etc.) are used. Here, the "human protein X" means that protein X has the amino acid sequence of protein X naturally expressed in human in vivo.

The factor for maintaining undifferentiated state to be used in the present invention is preferably isolated. Being "isolated" means that an operation to remove factors other than the intended component or cell has been performed, and the component or cell is no longer in a naturally occurring state. Therefore, "isolated protein X" does not include an endogenous protein X produced from the cells or tissue to be cultured, and contained in a cell or tissue or in the medium. The purity of the "isolated protein X" (percentage of the weight of protein X to the total protein weight) is generally not less than 70%, preferably not less than 80%, more preferably not less than 90%, further preferably not less than 99%, further preferably 100%. Therefore, in one embodiment, the present invention comprises a step of providing an isolated factor for maintaining undifferentiated state. In one embodiment, it includes a step of exogenously adding an isolated factor for maintaining undifferentiated state to a medium used in step (1). Alternatively, a factor for maintaining undifferentiated state may be added in advance to a medium to be used in step (1).

The concentration of the factor for maintaining undifferentiated state in the medium to be used in step (1) is a concentration capable of maintaining the undifferentiated state of the pluripotent stem cells to be cultured, and can be appropriately determined by those of ordinary skill in the art. For example, when bFGF is used as a factor for maintaining undifferentiated state in the absence of feeder cells, the concentration thereof is generally about 4 ng-500 ng/mL, preferably 10 ng-200 ng/mL, more preferably about 30 ng-150 ng/mL.

As the feeder-free medium, many synthetic media have been developed and are commercially available and, for example, Essential 8 medium can be mentioned. Essential 8 medium is DMEM/F12 medium containing L-ascorbic acid-2-phosphate magnesium (64 mg/l), sodium selenium (14 μg/l), insulin (19.4 mg/l), NaHCO$_3$ (543 mg/l), transferrin (10.7 mg/l), bFGF (100 ng/mL), and a TGFβ family signal transduction pathway activating substance (TGFβ 1 (2 ng/mL) or Nodal (100 ng/mL)) as additives (Nature Methods, 8, 424-429 (2011)). Examples of the commercially available feeder-free medium include Essential 8 (manufactured by Life Technologies), S-medium (manufactured by DS Pharma Biomedical), StemPro (manufactured by Life Technologies), hESF9 (Proc Natl Acad Sci USA. 2008 Sep. 9; 105(36):13409-14), mTeSR1 (manufactured by STEMCELL Technologies), mTeSR2 (manufactured by STEMCELL Technologies), and TeSR-E8 (manufactured by STEMCELL Technologies). In addition to these, StemFit (manufactured by Ajinomoto Co., Inc.) can be mentioned as the feeder-free medium. The present invention can be performed conveniently by using these in the above-mentioned step (1).

While a culture vessel used for adhesion culturing is not particularly limited as long as "adhesion culturing" can be performed, a cell adhesive culture vessel is preferable. Cell-adhesive culture vessels include culture vessels whose surfaces have been artificially treated to improve cell adhesiveness, and specifically, the above-mentioned surface-processed culture vessel, a culture vessel whose inside is coated with a coating agent can be mentioned. Examples of the coating agent include extracellular matrix such as laminin [including laminin α5β1γ1 (hereinafter laminin 511), laminin α1β1γ1 (hereinafter laminin 111) and the like and laminin fragment (laminin 511E8 etc.)], entactin, collagen, gelatin, vitronectin, Synthemax (Corning Incorporated), Matrigel and the like, or polymer such as polylysine, polyornithine and the like, and the like. It is also possible to use a culture container whose surface is processed by a positive electric charge treatment and the like. Preferred is laminin and more preferred is laminin 511E-8. Laminin 511E-8 can be a commercially available product (e.g., iMatrix-511, Nippi).

While the medium used for step (1) may be a serum-containing medium or a serum-free medium, it is preferably a serum-free medium, to avoid contamination with chemically-undefined components.

To avoid contamination with a chemically-undefined component, a medium to be used for step (1) may be a medium whose components are chemically-defined.

In step (1), the pluripotent stem cells may be cultured under any conditions of suspension culturing and adhesion culturing, preferably adhesion culturing.

For culturing pluripotent stem cells under feeder-free conditions in step (1), the aforementioned feeder-free medium can be used as a medium.

For culturing pluripotent stem cells under feeder-free conditions in step (1), an appropriate matrix may be used as a scaffold to provide a scaffold in stead of the feeder cells to the pluripotent stem cell. The pluripotent stem cells are subjected to adhesion culturing in a cell container whose surface is coated with a matrix as a scaffold.

As a matrix available as a scaffold, laminin (Nat Biotechnol 28, 611-615 (2010)), laminin fragment (Nat Commun 3, 1236 (2012)), basement membrane preparation (Nat Biotechnol 19, 971-974 (2001)), gelatin, collagen, heparan sulfate proteoglycan, entactin, vitronectin and the like can be mentioned.

"Laminin" is a heterotrimer molecule consisting of $\alpha$, $\beta$, $\gamma$ chains and an extracellular matrix protein containing isoforms having different subunit chain compositions. Specifically, laminin has about 15 kinds of isoforms based on the combinations of heterotrimers with 5 kinds of $\alpha$ chains, 4 kinds of $\beta$ chains and 3 kinds of $\gamma$ chains. The name of laminin is determined by combining respective numbers of $\alpha$ chain ($\alpha$1-$\alpha$5), $\beta$ chain ($\beta$1-$\beta$4) and $\gamma$ chain ($\gamma$1-$\gamma$4). For example, a laminin having a combination of $\alpha$5 chain, $\beta$1 chain, $\gamma$1 chain is named laminin 511. In the present invention, laminin 511 is preferably used (Nat Biotechnol 28, 611-615 (2010)).

Laminin to be used in the present invention is generally a mammalian laminin. As the mammal, those mentioned above can be recited. To achieve xeno-free conditions, laminin of a mammal of the same species as the cell to be cultured is preferably used. For example, human laminin (preferably, human laminin 511) is used for culturing human pluripotent stem cells.

A laminin fragment to be used in the present invention is not particularly limited as long as it has adhesiveness to pluripotent stem cells and enables maintenance culturing of pluripotent stem cell under feeder-free conditions, and is preferably E8 fragment. Laminin E8 fragment was identified as a fragment with strong cell adhesion activity among the fragments obtained by digestion of laminin 511 with elastase (EMBO J., 3:1463-1468, 1984, J. Cell Biol., 105:589-598, 1987). In the present invention, E8 fragment of laminin 511 is preferably used (Nat Commun 3, 1236 (2012), Scientific Reports 4, 3549 (2014)). The laminin E8 fragment to be used in the present invention is not required to be an elastase-digestion product of laminin and may be a recombinant. To avoid contamination of unidentified components, a recombinant laminin fragment is preferably used in the present invention. A E8 fragment of laminin 511 is commercially available and can be purchased from, for example, Nippi, Inc. and the like.

The laminin or laminin fragment to be used in the present invention is preferably isolated.

The "basement membrane preparation" in the present invention refers to one containing basement membrane-constituting components having a function to control cell morphology, differentiation, growth, motility, expression of function and so on which are similar to those of epithelial cell, when intended cells capable of forming a basement membrane are plated thereon and cultured. For example, neural cells and neural tissues produced by the present invention may be dispersed, and cultured in the presence of a basement membrane preparation when further adhesion culturing is performed. Here, the "basement membrane constituting components" refers to extracellular matrix molecules in the form of a thin membrane present between epithelial cell layer and interstitial cell layer and so on in animal tissues. A basement membrane preparation can be produced by, for example, removing cells capable of forming a basement membrane, which adhere onto a support via a basement membrane, from a support with a solution capable of dissolving the lipid of the cells, an alkali solution and so on. Examples of the basement membrane preparation include products commercially available as basement membrane preparation (e.g., Matrigel™ (manufactured by Corning Incorporated: hereinafter sometimes referred to as Matrigel)), Geltrex™ (manufactured by Life Technologies), and extracellular matrix molecules known as basement membrane components (e.g., laminin, type IV collagen, heparan sulfate proteoglycan, entactin and so on).

Matrigel™ is a basement membrane preparation extracted from Engelbreth Holm Swarn (EHS) mouse sarcoma. The main component of Matrigel™ is type IV collagen, laminin, heparan sulfate proteoglycan, and entactin. In addition to these, TGF-$\beta$, FGF, tissue plasminogen activator, and a growth factor naturally produced by EHS tumor are contained. The "growth factor reduced product" of Matrigel™ has a lower growth factor concentration than common Matrigel™, and the standard concentration thereof is <0.5 ng/ml for EGF, <0.2 ng/ml for NGF, <5 pg/ml for PDGF, 5 ng/ml for IGF1, and 1.7 ng/ml for TGF$\beta$.

To avoid contamination of unidentified components, an isolated laminin or laminin fragment is preferably used in the present invention.

Preferably, in the culturing of pluripotent stem cells under feeder-free conditions in step (1), the human pluripotent stem cells are cultured in an adhered state in a cell container with surface coated with isolated laminin 511 or E8 fragment of laminin 511 (more preferably, E8 fragment of laminin 511).

While the period for the culturing of pluripotent stem cells in step (1) is not particularly limited as long as the effect of improving the quality of the aggregate formed in step (2) can be achieved, it is generally 0.5-144 hr, preferably 2-96 hr, more preferably 6-48 hr, further preferably 12-48 hr, furthermore preferably 18-28 hr (e.g., 24 hr). That is, the first step is started 0.5-144 hr (preferably, 18-28 hr) before the start of step (2), and step (2) is continuously performed on completion of step (1).

In step (1), the medium may be changed as appropriate, and one embodiment specifically includes a method including medium change every 1-2 days. Here, for example, the medium may be changed with a medium free of the below-mentioned cell protecting agent or an agent suppressing cell death such as ROCK inhibitor and the like.

The culture conditions such as culture temperature, and $CO_2$ concentration in step (1) can be appropriately determined. While the culture temperature is, for example, about 30° C. to about 40° C., preferably about 37° C. The $CO_2$ concentration is, for example, about 1% to about 10%, preferably about 5%.

In one preferable embodiment, human pluripotent stem cells (e.g., human iPS cells) are cultured in an adhered state in the absence of feeder cells and in a serum-free medium containing bFGF. The adhesion culturing is preferably performed in a cell container with surface coated with laminin 511, E8 fragment of laminin 511 or vitronectin. The adhesion culturing is preferably performed using Essential 8, TeSR medium, mTeSR medium, mTeSR-E8 medium, or StemFit medium, more preferably Essential 8 or StemFit medium, as a feeder-free medium.

In one preferable embodiment, human pluripotent stem cells (e.g., human iPS cells) are cultured in suspension in the absence of feeder cells and in a serum-free medium containing bFGF. In the suspension culturing, human pluripotent stem cells may form an aggregate of human pluripotent stem cells.

Step (2) in which the pluripotent stem cells obtained in step (1) are cultured in suspension in the presence of a Sonic hedgehog signal transduction pathway activating substance to form a cell aggregate of pluripotent stem cells is explained.

The medium to be used in step (2) is not particularly limited as long as it is as described in the above-mentioned section of definition. The medium to be used in step (2) may be a serum-containing medium or serum-free medium. To avoid contamination of chemically-undefined components, a serum-free medium is preferably used in the present invention. For example, a serum-free medium free of a Wnt signal transduction pathway inhibiting substance can be used. To avoid complicated preparation, for example, a serum-free medium supplemented with an appropriate amount of a commercially available serum alternative such as KSR and so on (e.g., medium of 1:1 mixture of IMDM and F-12, which is supplemented with 10% KSR, 450 μM 1-monothioglycerol and 1× Chemically Defined Lipid Concentrate, or GMEM medium supplemented with 5%-20% KSR, NEAA, pyruvic acid, 2-mercaptoethanol) is preferably used. The amount of KSR to be added to a serum-free medium in the case of human ES cells is generally about 1% to about 30%, preferably about 2% to about 20%.

For formation of an aggregate, a dispersing operation of the pluripotent stem cells obtained in step (1) is first performed. The "dispersed cells" obtained by the dispersing operation refers to a state where, for example, not less than 70% of cells are single cells and not more than 30% of cells are clumps of 2-50 cells. Preferably, as the dispersed cells, a state where not less than 80% of cells are single cells, and not more than 20% of cells are clumps of 2-50 cells can be mentioned. The dispersed cells refer to a state almost free of mutual adhesion of cells (e.g., plane attachment). In a part of the embodiment, dispersed cells refer to a state almost free of cell-cell junction (e.g., adhesive bond).

A dispersion operation of the pluripotent stem cells obtained in step (1) may contain the above-mentioned mechanical dispersion treatment, cell dispersion solution treatment, and cell protecting agent addition treatment. These treatments may be performed in combination. Preferably, a cell dispersion solution treatment is performed simultaneously with a cell protecting agent addition treatment and then a is mechanical dispersion treatment is performed.

As a cell protecting agent to be used for the cell protecting agent addition treatment, a FGF signal transduction pathway activating substance, heparin, an IGF signal transduction pathway activating substance, serum, and serum alternative can be mentioned. Also, to suppress cell death of pluripotent stem cells (particularly, cell death of human pluripotent stem cells) induced by dispersion, and protect the cells, a Rho-associated coiled-coil kinase (ROCK) inhibitor or a Myosin inhibitor may be added. To suppress cell death of pluripotent stem cells (particularly, human pluripotent stem cells) induced by dispersion, a Rho-associated coiled-coil kinase (ROCK) inhibiting substance or a Myosin inhibitor may be added from the start of the second step culture. As a ROCK inhibiting substance, Y-27632, Fasudil (HA1077), H-1152 and the like can be mentioned. As a Myosin inhibitor, Blebbistatin can be mentioned.

As a cell dispersion solution to be used for the cell dispersion treatment, a solution containing any of enzymes such as trypsin, collagenase, hyaluronidase, elastase, pronase, DNase, papain and so on, and a chelating agent such as ethylenediaminetetraacetic acid and so on can be mentioned. A commercially available cell dispersion solution such as TrypLE Select (manufactured by Life Technologies) and TrypLE Express (manufactured by Life Technologies) can also be used.

As a method of mechanical dispersion treatment, a pipetting treatment or scraping by a scraper can be mentioned.

The dispersed cells are suspended in the above-mentioned medium.

Then, a suspension of the dispersed pluripotent stem cells is seeded in the above-mentioned culture vessel, and the dispersed pluripotent stem cells are cultured under a condition non-adhesive to the culture vessel, whereby plural cells are gathered to form an aggregate.

In this case, plural cell aggregates may be simultaneously formed in one culture vessel by seeding the dispersed pluripotent stem cells in a comparatively large culture vessel such as a 10 cm dish. However, the size of the aggregates varies in this case. Thus, for example, a given amount of dispersed pluripotent stem cells are placed in each well of a multiwell plate (U-bottom, V-bottom) such as a 96-well microplate, and static culture is performed, whereby the cells are rapidly coagulated to form one aggregate in each well. The aggregates are recovered from plural wells, whereby a population of uniformed aggregates can be obtained.

The concentration of the pluripotent stem cells in step (2) can be appropriately set so that cell aggregates can be more uniformly and efficiently formed. For example, when human cells (e.g., human iPS cells obtained in step (1)) are cultured in suspension using a 96-well microwell plate, a liquid prepared to achieve about $1\times10^3$ to about $1\times10^5$ cells, preferably about $3\times10^3$ to about $5\times10^4$ cells, more preferably about $4\times10^3$ to about $2\times10^4$ cells, further preferably about $4\times10^3$ to about $1.6\times10^4$ cells, further more preferably about $8\times10^3$ to about $1.2\times10^4$ cells, per well is added to the wells, and the plate is stood to form aggregates.

The culture conditions such as culture temperature, $CO_2$ concentration and so on in step (2) can be appropriately determined. The culture temperature is, for example, about 30° C. to about 40° C., preferably about 37° C. The $CO_2$ concentration is, for example, about 1% to about 10%, preferably about 5%.

In step (2), when a medium change operation is performed, for example, an operation to add a fresh medium without discarding the existing medium (medium addition operation), an operation to discard about a half amount of the existing medium (about 30-90%, for example, 40-60% of the volume of the existing medium) and add about a half amount of a fresh medium (30-90%, for example, about 40-60% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration (specifically 1.5 times-3.0 times the final concentration, for example, about 2 times the final concentration) (half-medium change operation) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cells or aggregates may be transferred to another culture container.

While the tool used for the medium change operation is not particularly limited, for example, pipetter, micropipette (PIPETMAN), multichannel micropipette (MULTICHANNEL PIPETMAN), continuous dispenser, and the like can be mentioned. For example, when a 96 well plate is used as a culture vessel, a multichannel micropipette (MULTICHANNEL PIPETMAN) may be used.

The period for suspension culturing necessary for forming a cell aggregate can be determined as appropriate according to the pluripotent stem cell to be used, so that the cells can be aggregated uniformly. To form uniformed cell aggregates, it is desirably as short as possible. The steps for the dispersed cells to form cell aggregates can be divided into a step for gathering cells, and a step for forming cell aggregates from the gathered cells. In a step of seeding the dispersed cells (i.e., at the time of the start of suspension culture) to gather the cells in case of human pluripotent stem cells (e.g., human iPS cells), for example, the gathered cells are formed preferably within about 24 hr, more preferably within about 12 hr. The period from the time point of seeding the dispersed cells (i.e., at the time of the start of suspension culture) to form an aggregate in the case of human pluripotent stem cells (e.g., human iPS cells), the aggregate is formed, for example, preferably within about 72 hr, more preferably within about 48 hr. The period for cell aggregate formation can be appropriately adjusted by controlling the tools for aggregating the cells, centrifugation conditions and so on.

Formation of cell aggregates and uniformity thereof can be determined based on the size and cell number of the aggregates, macroscopic morphology, microscopic morphology by tissue staining analysis and uniformity thereof, expression of differentiation- and undifferentiation-markers and uniformity thereof, control of expression of differentiation marker and synchronism thereof, reproducibility of differentiation efficiency between the aggregates, and so on.

After aggregate formation, the aggregate may be continuously cultured as it is. The period for suspension culturing in step (2) is generally about 12 hr-6 days, preferably about 12 hr-48 hr.

The medium used in step (2) contains a Sonic hedgehog signal transduction pathway activating substance. In step (1), pluripotent stem cells are subjected to maintenance culturing under feeder-free conditions; and in the second step, the pluripotent stem cells obtained in the first step are cultured in suspension in a medium (preferably serum-free medium) containing a Sonic hedgehog signal transduction pathway activating substance to improve quality of the aggregate, and a spherical, smooth surfaced, uncollapsed, and dense inside aggregate of cells maintaining undifferentiated properties can be formed at a high efficiency.

The Sonic hedgehog (hereinafter sometimes to be indicated as Shh) signal transduction pathway activating substance is a substance capable of enhancing signal transduction mediated by Shh. Examples of the Shh signal transduction pathway activating substance include proteins belonging to the Hedgehog family (e.g., Shh and Ihh), Shh receptor, Shh receptor agonist, Purmorphamine (PMA; 9-cyclohexyl-N-[4-(4-morpholinyl)phenyl]-2-(1-naphthalenyloxy)-9H-purin-6-amine), SAG (Smoothened Agonist; N-methyl-N'-(3-pyridinylbenzyl)-N'-(3-chlorobenzo[b]thiophene-2-carbonyl)-1,4-diaminocyclohexane) and the like. As the Shh signal transduction pathway activating substance, preferred are, for example, SAG, Purmorphamine (PMA) and Shh protein (Genbank accession numbers: NM_000193, NP_000184), and more preferred is SAG. The concentration of the Shh signal transduction pathway activating substance in the medium can be appropriately determined to fall within a range capable of achieving the aforementioned effects. SAG is generally used at a concentration of 1-2000 nM, preferably 10 nM-1000 nM, preferably 10 nM-700 nM, 30 nM-700 nM, 50 nM-700 nM, more preferably 100 nM-600 nM, further preferably 100 nM-500 nM. When an Shh signal transduction pathway activating substance other than SAG is used, it is desirably used at a concentration conferring Shh signal transduction promoting activity equivalent to that of SAG at the above-mentioned concentration. In the case of PMA, for example, the concentration generally corresponds to 0.002-20 μM, preferably 0.02-2 μM, further preferably about 0.2 μM; and in the case of Shh protein, for example, the concentration generally corresponds to about 10-1000 ng/ml, preferably about 10-300 ng/ml.

The concentration of the Sonic hedgehog signal transduction pathway activating substance in the medium may be varied during the period of step (2). For example, the Sonic hedgehog signal transduction pathway activating substance is provided to fall within the above-mentioned range at the time of the start of step (2), and the concentration may be gradually or stepwisely decreased at a ratio of 40-60% per 2-4 days.

The timing of addition of a Sonic hedgehog signal transduction pathway activating substance to the medium is not particularly limited as long as the above-mentioned effects can be afforded, but a higher effect can be obtained when it is added earlier. A Sonic hedgehog signal transduction pathway activating substance is added to the medium generally within 3 days, preferably within 2 days, more preferably within 1 day, from the start of step (2), and further preferably at the time of the start of step (2).

In a preferable embodiment, in step (2), the human pluripotent stem cells obtained in step (1) (e.g., human iPS cells) are subjected to suspension culturing in a serum-free medium containing a Sonic hedgehog signal transduction pathway activating substance (e.g., SAG, Shh protein, PMA) to form aggregates. A Sonic hedgehog signal transduction pathway activating substance is preferably contained in the medium from the time of the start of suspension culture. A ROCK inhibiting substance (e.g., Y-27632) may also be added to the medium. The period for the culturing is 12 hr-6 days, preferably 12 hr-48 hr. The aggregates formed are preferably uniformed aggregates.

For example, the human pluripotent stem cells obtained in step (1) (e.g., human iPS cells) are recovered, dispersed into single cells or a state close thereto, suspended in a serum-free medium containing a Sonic hedgehog signal transduction pathway activating substance (e.g., SAG, Shh protein, PMA), and subjected to suspension culturing. The serum-free medium may contain a ROCK inhibiting substance (e.g., Y-27632). A suspension of human pluripotent stem cells (e.g., iPS cells) is seeded in the above-mentioned culture vessel and the dispersed pluripotent stem cells are cultured under conditions where they are non-adhesive to the culture vessel, whereby plural pluripotent stem cells are assembled to form an aggregate. The period for the culturing is 12 hr-6 days, preferably 12 hr-48 hr. The aggregates formed are preferably uniformed aggregates.

By performing step (2) in this manner, an aggregate of the pluripotent stem cells obtained in step (1), or the cells derived therefrom are formed. The present invention also provides a method for producing such aggregate. The aggregate obtained in step (2) has higher quality than the one formed by a treatment with a Sonic hedgehog signal transduction pathway activating substance is not performed in step (2). To be specific, a population of aggregates having a high ratio of spherical cell aggregates having a smooth surface, a dense inside, and uncollapsed shape can be obtained. In one embodiment, when aggregates (e.g., not less than 100 aggregates) are randomly selected on day 6 from the start of the second step, the sum of the ratios of uncollapsed aggregates and/or non-cystic aggregates is, for example, not less than 30%, preferably not less than 50%.

The aggregate obtained in step (2) has a potency to differentiate into various differentiated cells and differentiated tissues. In one embodiment, the aggregate obtained in step (2) has a potency to differentiate into a neural cell (e.g., retinal cell) or a neural tissue (e.g., retinal tissue). In one embodiment, by using the stem cells obtained in step (1) and having a potency to differentiate into at least a neural cell or a neural tissue (preferably, retinal tissue, retinal progenitor cell, or retinal layer-specific neuron) (preferably, Oct3/4 positive stem cells having a potency to differentiate into at least a neural cell or a neural tissue (preferably, retinal tissue, retinal progenitor cell, or retinal layer-specific neuron)) in step (2), an aggregate containing stem cells (e.g., Oct3/4 positive stem cells) having a potency to differentiate into at least a neural cell or a neural tissue (preferably, retinal tissue, retinal progenitor cell, or retinal layer-specific neuron) can be obtained. Various differentiated cells and differentiated tissues (e.g., neural cells such as retinal cells etc., neural tissues such as retinal tissue etc.) can be induced with high efficiency by culturing the aggregate obtained in step (2) under appropriate differentiation conditions.

In one embodiment, the aggregate obtained in step (2) contains cells corresponding to the cells in an intermediate stage between the pluripotent stem cells obtained in step (1), and neural cells or a neural tissue (preferably, retinal cells or a retinal tissue). These cells express any of pluripotent state marker Oct3/4, ectoderm marker (Sox1, Sox2, N-cadherin, TP63), neuroectoderm marker (Sox1, Sox2, Nestin, N-cadherin, Otx2), and the aforementioned neural cell marker. That is, in one embodiment, the aggregate obtained in step (2) contains a mixture of cells expressing any of pluripotent state marker Oct3/4, ectoderm marker (Sox1, Sox2, N-cadherin, TP63), neuroectoderm marker (Sox1, Sox2, Nestin, N-cadherin, Otx2), and the aforementioned neural cell marker. That is, the aggregate obtained in step (2) contains stem cells having a potency to differentiate into at least a neural cell or neural tissue (preferably, retinal cell or retinal tissue), and/or progenitor/precursor cells of a neural cell or neural tissue (preferably, retinal cell or retinal tissue). In addition, the progenitor/precursor cells are characterized in that they show an ability (competence) to express the aforementioned neural cell markers (preferably, retinal cell marker) when they are cultured under known appropriate culture conditions. Therefore, in one embodiment, the aggregate obtained in step (2) contains Oct3/4 positive stem cells having a potency to differentiate into at least a neural cell or neural tissue (preferably, retinal cell or retinal tissue), and/or progenitor/precursor cells of a neural cell or neural tissue (preferably, retinal cell or retinal tissue). A part of the cells contained in the aggregate obtained in step (2) may express the aforementioned neural tissue markers. In one embodiment, the aggregate obtained in step (2) may contain Oct3/4 positive cells at a proportion of not less than 50%, for example, not less than 70%, of the total cells.

In step (2), when a medium change operation is performed, for example, an operation to add a fresh medium without discarding the existing medium (medium addition operation), an operation to discard about a half amount of the existing medium (about 30-90%, for example, about 40-60% of the volume of the existing medium) and add about a half amount of a fresh medium (about 30-90%, for example, about 40-60% of the volume of the existing medium) (half-medium change operation), and an operation to discard about the whole amount of the existing medium (not less than 90% of the amount of the existing medium) and add about the whole amount of a fresh medium (not less than 90% of the amount of the existing medium) (full-medium change operation) can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration (specifically 1.5-3.0 times the final concentration, for example, about 2 times the final concentration) (half-medium change operation) may be performed.

When the concentration of a particular component contained in the existing medium is maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture vessel.

While the tool used for the medium change operation is not particularly limited, for example, pipetter, micropipette (PIPETMAN), multichannel micropipette (MULTICHANNEL PIPETMAN), continuous dispenser, and the like can be mentioned. For example, when a 96 well plate is used as a culture vessel, a multichannel micropipette (MULTICHANNEL PIPETMAN) may be used.

Step (3) where an aggregate containing retinal cells or a retinal tissue are induced from the aggregate obtained in step (2) is explained.

The aggregate obtained in step (2) is cultured in suspension in the presence or absence (preferably in the presence) of an appropriate differentiation-inducing factor, whereby an aggregate containing retinal cells or a retinal tissue can be obtained.

As a method for inducing an aggregate of cells into retinal cells or a retinal tissue by suspension culturing, many methods have been reported. For example, the methods described in Nature, 472, 51-56 (2011), Cell Stem Cell, 10(6), 771-775 (2012) and the like are known, though the method is not limited thereto.

As a method for producing retinal cells or a retinal tissue in the absence of a differentiation-inducing factor, a method comprising inducing spontaneous differentiation of the aggregates obtained in step (2) into neural cells including retinal cells in a serum-containing medium or serum-free medium can be mentioned. As the aforementioned serum-containing medium or serum-free medium, a serum medium or serum-free medium free of a factor for maintaining undifferentiated state can be mentioned. Retinal cells produced during the process of differentiation into neural cells may be selected and isolated. For selection and isolation, FACS or MACS may be used. In addition, pluripotent stem cells, which easily produce retina, may also be used as a starting material in step (1).

Preferably, the aggregate obtained in step (2) is cultured in suspension in the presence of a differentiation-inducing factor to give an aggregate containing retinal cells or a retinal tissue.

The differentiation-inducing factor used here is not particularly limited as long as it is a factor having an activity to induce differentiation into a retinal cell or retinal tissue. Examples thereof include a BMP signal transduction activating substance, basement membrane preparation, a Wnt signal transduction pathway inhibiting substance, a TGFβ family signal transduction pathway inhibiting substance and the like. Responses to a differentiation-inducing factor vary depending on the kind and differentiation state (competence or potential) of the cell, and the effect of the differentiation-inducing factor may vary even in the differentiation induction process, depending on the concentration and timing of addition of the differentiation-inducing factor. Also, it is known that the optimal concentration of a differentiation-inducing factor that exhibits similar effects varies depending on the animal species and, for example, it is known that, between mouse cell and human cell, the optimal concentration of human cell is generally higher (particularly in ectoderm, endoderm). There are many reports on the methods of differentiation induction of pluripotent stem cells into particular cells or tissues, and a differentiation-inducing factor or a differentiation induction method suitable for the intended cell or tissue can be selected.

Preferably, a BMP signal transduction pathway activating substance is used as a differentiation-inducing factor. That is, the aggregate obtained in step (2) is cultured in suspension in the presence of a BMP signal transduction pathway activating substance to give an aggregate containing retinal cells or a retinal tissue.

The BMP signal transduction pathway activating substance is a substance capable of enhancing signal transduction mediated by BMP. Examples of the BMP signal transduction pathway activating substance include BMP proteins such as BMP2, BMP4, BMP7 etc., GDF proteins such as GDF7 etc., anti-BMP receptor antibody, BMP partial peptide and so on. BMP2 protein, BMP4 protein and BMP7 protein are available from, for example, R&D Systems, and GDF7 protein is available from, for example, Wako Pure Chemical Industries, Ltd. The BMP signal transduction pathway activating substance is preferably BMP4.

The differentiation-inducing factor (e.g., BMP4) to be used in the present invention is generally a mammalian differentiation-inducing factor. Examples of the mammal include those mentioned above. Since differentiation-inducing factor may have cross-reactivity among mammalian species, differentiation-inducing factor of any mammal may also be used as long as differentiation induction of the cultured pluripotent stem cell can be achieved. Preferably, a mammalian differentiation-inducing factor of the same species as the cell to be cultured is used. For example, when differentiation of human pluripotent stem cells into a retinal tissue or retinal cell is induced, a human differentiation-inducing factor (e.g., BMP4) is preferably used.

The differentiation-inducing factor (e.g., BMP4) used in the present invention is preferably isolated. Therefore, in one embodiment, the present invention comprises a step of providing an isolated differentiation-inducing factor (e.g., BMP4). In one embodiment, moreover, the present invention comprises a step of exogenously adding the isolated differentiation-inducing factor (e.g., BMP4) to the medium to be used in step (3).

In one embodiment, the medium to be used in step (3) is a serum-free medium or a serum-containing medium (preferably serum-free medium) supplemented with a differentiation-inducing factor (e.g., BMP4). Such medium may or may not contain a basement membrane preparation. As the basement membrane preparation, those mentioned above can be used. When a basement membrane preparation is added, the concentration thereof is, for example, 0.1 to 10%, more preferably 0.5% to 2%, in volume concentration when Matrigel is used. To avoid contamination with a chemically unidentified substance, a basement membrane preparation is not added.

A serum-free medium or serum-containing medium to be used for such medium is not particularly limited as long as it is as mentioned above. To avoid complicated preparation, for example, a serum-free medium supplemented with an appropriate amount of a commercially available serum alternative such as KSR and so on (e.g., medium of 1:1 mixture of IMDM and F-12 supplemented with 10% KSR, 450 μM 1-monothioglycerol and 1× Chemically Defined Lipid Concentrate or a medium of GMEM supplemented with 5%-20% KSR, NEAA, pyruvic acid, 2-mercaptoethanol) is preferably used. The amount of KSR to be added to a serum-free medium in the case of human ES cells is generally about 1% to about 20%, preferably about 2% to about 20%.

As the medium (preferably serum-free medium) to be used in step (3), the medium (preferably serum-free medium) used in step (2) may be directly used, or may be replaced with a fresh medium (preferably serum-free medium). When the serum-free medium used in step (2) free of differentiation-inducing factor (e.g., BMP4) is directly used for step (3), a differentiation-inducing factor (e.g., BMP4) may be added to the medium.

In one embodiment, when the concentration of the Shh signal transduction pathway activating substance added to the medium in step (2) is comparatively low (e.g., not more than 700 nM for SAG, and a concentration conferring Shh signal transduction promoting activity equivalent to or lower than that of SAG at the above-mentioned concentration, for other Shh signal transduction pathway activating substances), medium change is not necessary, and a differentiation-inducing factor (e.g., BMP4) may be added to the medium used in step (2). On the other hand, when the concentration of the Shh signal transduction pathway activating substance is comparatively high (e.g., exceeding 700 nM or not less than 1000 nM for SAG, and a concentration conferring a Shh signal transduction promoting activity equivalent to that of SAG at the above-mentioned concentration, for other Shh signal transduction pathway activating substances), it is desirable to change the medium to a fresh medium containing a differentiation-inducing factor (e.g., BMP4) to suppress an influence of the Shh signal transduction pathway activating substance remaining when a differentiation-inducing factor is added.

In a preferable embodiment, the concentration of a Shh signal transduction pathway activating substance in the medium to be used in step (3) is, when calculated in terms of Shh signal transduction promoting activity of SAG, not more than 700 nM, preferably not more than 300 nM, more preferably not more than 10 nM, further preferably not more than 0.1 nM, further preferably free of a Shh signal transduction pathway activating substance. The medium "free of a Shh signal transduction pathway activating substance" also includes a medium substantially free of a Shh signal transduction pathway activating substance, for example, a medium free of a Shh signal transduction pathway activating substance at a concentration imparting an adverse influence on selective differentiation into a retinal cell or a retinal tissue. The medium "free of a Shh signal transduction pathway activating substance" also includes a medium substantially not supplemented with a Shh signal transduction pathway activating substance, for example, a medium not supplemented with a Shh signal transduction pathway activating substance at a concentration imparting an adverse influence on selective differentiation into a retinal cell or a retinal tissue.

The concentration of the differentiation-inducing factor (e.g., BMP signal transduction pathway activating substance) in the medium may be a concentration at which differentiation of the aggregate of pluripotent stem cells or cells derived therefrom, into retinal cells can be induced. For example, in the case of human BMP4, it is added to the medium to a concentration of about 0.01 nM to about 1 μM, preferably about 0.1 nM to about 100 nM, more preferably about 1 nM to about 10 nM, further preferably about 1.5 nM (55 ng/mL). When a BMP signal transduction pathway activating substance other than BMP4 is used, it is desirably used at a concentration at which a BMP signal transduction promoting activity equivalent to that of BMP4 at the above-mentioned concentration is exerted.

The concentration of the differentiation-inducing factor (e.g., BMP4) in the medium may be varied during the period of step (3). For example, the differentiation-inducing factor (e.g., BMP4) is provided to fall within the above-mentioned range at the time of the start of step (3), and the concentration may be gradually or stepwisely decreased at a ratio of 40-60% per 2-4 days.

A differentiation-inducing factor (e.g., BMP4) may be added after about 24 hr or later from the start of the suspension culturing in step (2), and may also be added to the medium within several days (e.g., within 15 days) from the start of the suspension culturing. Preferably, a differentiation-inducing factor (e.g., BMP4) is added to the medium within day 1 to day 15, more preferably within day 1 to day 9, further preferably within day 3 to day 8, still more preferably, within day 3 to day 6, from the start of the suspension culture.

After the addition of a differentiation-inducing factor (e.g., BMP4) to the medium and the start of the differentiation induction of aggregate into retinal cells, addition of the differentiation-inducing factor (e.g., BMP4) to the medium is not necessary, and the medium may be exchanged with a serum-free medium or serum-containing medium each free of a differentiation-inducing factor (e.g., BMP4). In one embodiment, after the start of the differentiation induction of the aggregate into neural cells, the concentration of the differentiation-inducing factor (e.g., BMP4) in the medium is gradually or stepwisely decreased at a ratio of 40-60% per 2-4 days by exchanging the medium with a serum-free medium or a serum-containing medium, each free of a differentiation-inducing factor (e.g., BMP4). As a result, the concentration of a differentiation-inducing factor (e.g., BMP4) can be stepwisely diluted and the effect and the duration of action of the differentiation-inducing factor can be limited.

In a specific embodiment, the medium may be partly or entirely exchanged with a medium containing BMP4 on day 1-9, preferably day 2-8, further preferably day 3 or 4, after the start of suspension culturing (i.e., after the start of the aforementioned step (2)) to adjust the final concentration of BMP4 to about 1-10 nM, and the cells may be cultured in the presence of BMP4 for about 1-12 days, preferably 2-9 days, more preferably 2-5 days. To maintain the concentration of BMP4 at the same level, the medium may be partly or entirely exchanged one or two times with a medium containing BMP4. Alternatively, as mentioned above, the concentration of BMP4 may also be stepwisely reduced.

The cells in which induction of differentiation into retinal cells has been started can be confirmed by, for example, detecting the expression of retinal progenitor cell marker gene (e.g., Rx gene (alias Rax), Pax6 gene, Chx10 gene) in the cells. The aggregate formed in step (2) by using pluripotent stem cells in which a fluorescence reporter protein gene such as GFP and so on is knocked-in into the Rx gene locus is cultured in suspension in the presence of a differentiation-inducing factor (e.g., BMP4) at a concentration necessary for differentiation induction into retinal cell, and fluorescence emitted from the expressed fluorescence reporter protein is detected, whereby the time point when differentiation induction into retinal cell was started can be confirmed. As one embodiment of step (3), a step of culturing the aggregate formed in step (2) in suspension in a serum-free medium or serum-containing medium containing a differentiation-inducing factor (e.g., BMP4) at a concentration necessary for differentiation induction into retinal cell, until a cell expressing retinal progenitor cell marker gene (e.g., Rx gene, Pax6 gene, Chx10 gene) begins appearing, thereby obtaining a cell aggregate comprising retinal progenitor cells.

In step (3), when a medium change operation is performed, for example, medium addition operation, half-medium change operation and full-medium change operation can be mentioned.

When a particular component (e.g., differentiation-inducing factor) is added at a certain time point, for example, an operation to calculate the final concentration, to discard about a half amount of the existing medium, and to add about a half amount of a fresh medium containing a particular component at a concentration higher than the final concentration (specifically 1.5-3.0 times the final concentration, for example, about 2 times the final concentration) (half-medium change operation) may be performed.

When the concentration of a particular component contained in the existing medium is to be maintained at a certain time point, for example, an operation to discard about a half amount of the existing medium and to add about a half amount of a fresh medium containing the particular component at a concentration same as that in the existing medium may be performed.

When the concentration of a component contained in the existing medium is to be decreased by dilution at a certain time pointed, for example, the medium change operation may be performed plural times per day, preferably plural times (e.g., 2-3 times) within 1 hr. Also, when the concentration of a component contained in the existing medium is to be decreased by dilution at a certain time point, the cell or aggregate may be transferred to another culture container.

While the tool used for the medium change operation is not particularly limited, for example, pipetter, micropipette (PIPETMAN), multichannel micropipette (MULTICHANNEL PIPETMAN), continuous dispenser, and the like can be mentioned. For example, when a 96 well plate is used as a culture vessel, a multichannel micropipette (MULTICHANNEL PIPETMAN) may be used.

The culture conditions such as culture temperature, $CO_2$ concentration and so on in step (3) can be appropriately determined. The culture temperature is, for example, about 30° C. to about 40° C., preferably about 37° C. The $CO_2$ concentration is, for example, about 1% to about 10%, preferably about 5%.

By such culturing, differentiation of the cells forming the aggregate obtained in step (2) into retinal progenitor cells is induced, whereby an aggregate containing the retinal progenitor cells can be obtained. The present invention also provides a method for producing such aggregate containing retinal progenitor cell. That an aggregate comprising retinal progenitor cells was obtained can be confirmed by, for example, detecting the presence of cells expressing Rax, PAX6 or Chx10, which is a retinal progenitor cell marker, in the aggregate. One embodiment of step (3) is a step of culturing the aggregate formed in step (2) in suspension in a serum-free medium or serum-containing medium containing a BMP signal transduction pathway activating substance (e.g., BMP4) at a concentration necessary for differentiation induction into retinal cell, until a cell expressing Rx gene begins appearing, whereby obtaining an aggregate comprising retinal progenitor cells. In one embodiment, the culturing of step (3) is performed until not less than 20% (preferably, not less than 30%, not less than 40%, not less than 50%, not less than 60%) of the cells contained in the aggregate express Rx.

The obtained aggregate containing retinal progenitor cells may be used as it is as a reagent for evaluating toxicity or efficacy. An aggregate containing retinal progenitor cells is subjected to a dispersion treatment (e.g., trypsin/EDTA treatment or papain treatment), and the obtained cells are subjected to a selection using FACS or MACS, whereby highly pure retinal progenitor cells can also be obtained.

Furthermore, the aggregate containing retinal tissue may be continuously cultured in a serum-free medium or serum-containing medium to make retinal cells (e.g., retinal progenitor cells) contained in the retinal tissue to further differentiate, whereby a neuroepithelial structure-like retinal tissue may be produced.

A serum-free medium or serum-containing medium to be used for such medium is not particularly limited as long as it is as mentioned above. For example, a serum-containing medium which is a DMEM-F12 medium supplemented with 10% fetal bovine serum, N2 supplement, 100 μM taurine, and 500 nM retinoic acid, or a serum-free medium supplemented with an appropriate amount of a commercially available serum alternative such as KSR and so on (e.g., medium of 1:1 mixture of IMDM and F-12 supplemented with 10% KSR, 450 μM 1-monothioglycerol and 1× Chemically Defined Lipid Concentrate) and the like can be mentioned.

While the period for the culturing for inducing a retinal tissue from retinal progenitor cells varies depending on the intended retinal layer-specific neuron, it is, for example, about 7 days to about 200 days.

The retinal tissue exists covering the surface of the aggregate. After completion of the suspension culturing, the aggregate may be fixed with a fixative such as para-formaldehyde solution and so on, and a cryosection is prepared, then formation of a retinal tissue having a layer structure may be confirmed by immunostaining and the like. Since respective layers of a retinal tissue are composed of different cells (photoreceptor cell, horizontal cell, bipolar cell, amacrine cell, retinal ganglion cell), formation of a layer structure can be confirmed using antibodies against the aforementioned markers expressed in these cells by the immunostaining. In one embodiment, the retinal tissue is a Rx- or Chx10-positive neuroepithelial structure.

The retinal tissue existing on the surface of the aggregate can be physically cut out from the aggregate by using tweezers and the like. In this case, since a neural tissue other than the retinal tissue may be formed on the surface of each aggregate, a part of the neural tissue cut out from the aggregate may be subjected to confirmation by the below-mentioned immunostaining and the like, whereby the tissue can be confirmed to be a retinal tissue.

In one embodiment, the aggregate obtained in step (3) contains a retinal tissue and is substantially free of non-neural head ectoderm. In an aggregate containing a retinal tissue and substantially free of non-neural head ectoderm, for example, Rx-positive tissue is observed and an Rx-negative tissue is not observed on the outside thereof in the immunostaining images of the aforementioned aggregate frozen section.

One embodiment of step (3) is a step of culturing the aggregate formed in step (2) in suspension in a serum-free medium or serum-containing medium containing a BMP signal transduction pathway activating substance at a concentration necessary for differentiation induction into retinal cells, until a cell expressing Rx gene begins appearing to give an aggregate comprising retinal progenitor cells, and subsequently culturing the aggregate containing the retinal progenitor cells in suspension in a serum-free medium or serum-containing medium until a retinal tissue is formed, whereby obtaining an aggregate comprising a retinal tissue. When the aggregate containing the retinal progenitor cells is subsequently cultured in suspension in a serum-free medium or serum-containing medium until a retinal tissue is formed, the concentration of the BMP signal transduction pathway activating substance in the medium in order to induce retinal progenitor cells may be gradually or stepwisely decreased at a ratio of 40-60% per 2-4 days by exchanging the medium with a serum-free medium or a serum-containing medium, each free of a BMP signal transduction pathway activating substance. In one embodiment, suspension culturing of an aggregate containing retinal progenitor cells is performed until not less than 20% (preferably, not less than 30%, not less than 40%, not less than 50%, not less than 60%) of the cells contained in the aggregate expresses Chx10.

In one embodiment of step (3), the aggregate obtained in step (2), or an aggregate obtained by culturing the aggregate obtained in step (2) in suspension by the above-mentioned method may be subjected to adhesion culturing to form an adhered aggregate. The adhered aggregate is cultured in an adhered state in a serum-free medium or serum-containing medium containing a differentiation-inducing factor (e.g., BMP4) at a concentration necessary for differentiation induction into a retinal cell, until a cell expressing Rx gene begins appearing to give an adhered aggregate containing retinal progenitor cells. The aggregate containing the retinal progenitor cells is cultured in an adhered state in a serum-free medium or serum-containing medium until a retinal tissue is formed, whereby an adhered aggregate containing a retinal tissue is obtained. In one embodiment, adhesion culturing of the adhered aggregate containing retinal progenitor cells is performed until not less than 10% (preferably, not less than 20%, not less than 30%, not less than 40%, not less than 50%) of the cells express Chx10.

By the method of the present invention, retinal cells and a retinal tissue can be obtained from pluripotent stem cells with high efficiency. Since the retinal tissue obtained by the method of the present invention contains neurons (neuronal cell) specific to each of the retinal layers, it is also possible to obtain various cells constituting a retinal tissue, such as photoreceptor cell, horizontal cell, bipolar cell, amacrine cell, retinal ganglion cell or a progenitor/precursor cell thereof and the like. Which cell was obtained from the obtained retinal tissue can be confirmed by a method known per se, for example, expression of a cell marker.

The obtained aggregate containing a retinal tissue may also be directly used as a reagent for evaluating toxicity or efficacy. An aggregate containing a retinal tissue is subjected to a dispersion treatment (e.g., trypsin/EDTA treatment), and the obtained cells are subjected to a selection using FACS or MACS, whereby highly pure retinal tissue-constituting cells, for example, highly pure photoreceptor cells, can also be obtained.

A ciliary marginal zone-like structure can be produced by the following step (A) and step (B) from the cell aggregate containing a retinal tissue, which is obtained by the production method of the present invention.

The ciliary marginal zone-like structure refers to a structure similar to a ciliary marginal zone. Examples of the "ciliary marginal zone (CMZ)" include a tissue present in the boundary region of retinal tissue (specifically, neural retina) and retinal pigment epithelium in the retina in vivo, which is a region containing tissue stem cells of retina (retinal stem cells). Ciliary marginal zone is also called a ciliary margin or retinal margin, and the ciliary marginal zone, ciliary margin and retinal margin are equivalent tissues. It is known that the ciliary marginal zone plays an important role in the supply of retinal progenitor cells or differentiated cells to retinal tissues, maintenance of retinal tissue structure and so on. Examples of the marker gene of the ciliary marginal zone include Rdh10 gene (positive), Otx1 gene (positive), Zic1 gene (positive) and so on.

Step (A) comprises culturing a cell aggregate comprising a retinal tissue obtained by the production method 2 of the present invention in which Chx10 positive cells are present in a proportion of 20% or more and 100% or less of the retinal tissue, in a serum-free medium or serum-containing medium each containing a Wnt signal pathway activating substance and/or a FGF signal pathway inhibiting substance for only a period before the appearance of a RPE65 gene-expressing cell.

As a preferable culturing of step (A) here, suspension culturing can be mentioned.

As a serum-free medium to be used in step (A), a serum-free medium which is a basal medium supplemented with N2 or KSR can be mentioned. More specifically, a serum-free medium which is a DMEM/F-12 medium supplemented with N2 supplement (N2, manufactured by Life Technologies) can be mentioned. As the serum-containing medium, a serum-containing medium which is a basal medium supplemented with fetal bovine serum can be mentioned.

The culture conditions of step (A) such as culture temperature, $CO_2$ concentration can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

In step (A), the Wnt signal transduction pathway activating substance to be contained in a serum-free medium or serum-containing medium when the above-mentioned "cell aggregate comprising a retinal tissue" is cultured in the medium is not particularly limited as long as it can enhance signal transduction mediated by Wnt. Specific examples of the Wnt signal transduction pathway activating substance include a protein belonging to Wnt family (e.g., Wnt1, Wnt3a, Wnt7a), Wnt receptor, Wnt receptor agonist, GSK3 inhibitor (e.g., 6-Bromoindirubin-3'-oxime (BIO), CHIR99021, Kenpaullone) and so on.

The concentration of the Wnt signal transduction pathway activating substance to be contained in a serum-free medium or serum-containing medium in step (A) in the case of a common Wnt signal transduction pathway activating substance such as CHIR99021 is, for example, in the range of about 0.1 μM to about 100 μM, preferably, for example, in the range of about 1 μM to about 30 μM, more preferably, for example, around 3 μM.

The FGF signal transduction pathway inhibiting substance to be contained in a serum-free medium or serum-containing medium in step (A) when the above-mentioned "cell aggregate comprising a retinal tissue" is cultured in the medium is not particularly limited as long as it can inhibit signal transduction mediated by FGF. Examples of the FGF signal transduction pathway inhibiting substance include FGF receptor, FGF receptor inhibitor (e.g., SU-5402, AZD4547, BGJ398), MAP kinase cascade inhibiting substance (e.g., MEK inhibitor, MAPK inhibitor, ERK inhibitor), PI3 kinase inhibitor, Akt inhibitor and so on.

The concentration of the FGF signal transduction pathway inhibiting substance contained in a serum-free medium or serum-containing medium in step (A) only needs to be a concentration at which differentiation of an aggregate into ciliary marginal zone-like structure can be induced. For example, in the case of SU-5402, it is added to the medium to a concentration of about 0.1 μM to about 100 μM, preferably about 1 μM to about 30 μM, more preferably about 5 μM.

"Culturing for only a period before the appearance of a RPE65 gene-expressing cell" in step (A) means culturing in the whole or a part of the period before the appearance of a RPE65 gene-expressing cell. That is, culturing in the whole or a part of the period (any period) during which the aforementioned "cell aggregate comprising a retinal tissue" in the culture system is constituted by cells that do not substantially express RPE65 gene suffices. By employing such culturing, a cell aggregate in which a RPE65 gene-expressing cell does not appear can be obtained.

To determine such particular period, the aforementioned "cell aggregate comprising a retinal tissue" is used as a sample, and the presence or absence of expression of RPE65 gene contained in the sample or the level thereof may be measured by a general genetic engineering method or a biochemical method. Specifically, for example, the presence or absence of expression of RPE65 gene or the level thereof can be examined by subjecting a cryosection of the aforementioned "cell aggregate comprising a retinal tissue" to an immunostaining method using an antibody against RPE65 protein.

As a "period before the appearance of a RPE65 gene-expressing cell" in step (A), for example, a period during which the ratio of Chx10 positive cells present in the above-mentioned retinal tissue decreases than that at the time of start of the culturing of the aforementioned cell aggregate in a serum-free medium or serum-containing medium each containing a Wnt signal transduction pathway activating substance and/or a FGF signal transduction pathway inhibiting substance, and falls within the range of 30% to 0% can be mentioned. As the "cell aggregate in which a RPE65 gene-expressing cell does not appear", a cell aggregate in which Chx10 positive cells are present in the above-mentioned retinal tissue in a proportion of within 30% to 0% of the tissue can be mentioned.

While the number of days of the "period before the appearance of a RPE65 gene-expressing cell" in step (A) varies depending on the kind of the Wnt signal transduction pathway activating substance and/or the FGF signal transduction pathway inhibiting substance, the kind of the serum-free medium or serum-containing medium, other culture conditions and so on, it is, for example, within 14 days. More specifically, when a serum-free medium (e.g., serum-free medium which is a basal medium supplemented with N2) is used, the above-mentioned period is preferably, for example, within 10 days, more preferably, for example, 3 days to 6 days. When a serum-containing medium (e.g., serum-containing medium which is a basal medium supplemented with fetal bovine serum) is used, the aforementioned period is preferably, for example, within 12 days, more preferably, for example, 6 days to 9 days.

Then as step (B), the "cell aggregate in which a RPE65 gene-expressing cell does not appear" obtained by culturing as mentioned above is cultured in a serum-free medium or serum-containing medium each free of a Wnt signal transduction pathway activating substance.

As a preferable culturing in step (B), suspension culturing can be mentioned.

As the serum-free medium in step (B), a medium which is a basal medium supplemented with N2 or KSR can be mentioned. As the serum-containing medium, a medium which is a basal medium supplemented with fetal bovine serum can be mentioned. More specifically, a serum-containing medium which is a DMEM/F-12 medium supplemented with fetal bovine serum can be mentioned.

The above serum-free medium or serum-containing medium in step (B) may contain a known growth factor, an additive and a chemical substance that promote the growth, and so on. Examples of the known growth factor include EGF, FGF, IGF, insulin and so on. Examples of the additive that promotes the growth include N2 supplement (Life Technologies), B27 supplement (Life Technologies), KSR and so on. Examples of the chemical substance that promotes the growth include retinoids (e.g., retinoic acid) and taurine.

A preferable period for the culturing in step (B) is, for example, a period for the culturing during which the ratio of Chx10 positive cells present in the above-mentioned retinal tissue increases than that at the time of start of the culturing of the aforementioned cell aggregate in a serum-free medium or serum-containing medium each free a Wnt signal transduction pathway activating substance, and reaches 30% or more.

The culture conditions such as culture temperature, $CO_2$ concentration and the like in step (B) can be appropriately set. The culture temperature is, for example, in the range of about 30° C. to about 40° C., preferably, for example, around about 37° C. The $CO_2$ concentration is, for example, in the range of about 1% to about 10%, preferably, for example, around about 5%.

While the number of the above-mentioned culture days until "a cell aggregate comprising a ciliary marginal zone-like structure" is obtained in step (B) varies depending on the kind of the serum-free medium or serum-containing medium, other culture conditions and so on, it is, for example, within 100 days. The above number of culture days is preferably, for example, 20 days to 70 days, more preferably, for example, 30 days to 60 days.

In a "cell aggregate comprising a ciliary marginal zone-like structure" prepared by the aforementioned step (A), (B), a retinal pigment epithelium and a retinal tissue (specifically, neural retina) are present adjacent to the ciliary marginal zone-like structure in the same cell aggregate. The structure can be confirmed by microscopic observation and so on. Specifically, for example, the presence of a ciliary marginal zone-like structure as an epithelial structure having a thick retina side and a thin retinal pigment epithelium side, which is formed between a retinal tissue having high transparency and retinal pigment epithelium showing pigmentation, can be confirmed by microscopic observation. In addition, the presence of ciliary marginal zone-like structure can be confirmed by identifying Rdh10 positive, Otx1 positive, or Zic1 positive cells with immunostaining a frozen section of aggregate.

A retinal pigment epithelial cell can be produced by the following step (C) from a cell aggregate containing a retinal tissue obtained by the production method of the present invention and the like. A retinal pigment epithelial sheet can be produced by the following step (D) from a retinal pigment epithelial cell obtained by the following step (C).

The "retinal pigment epithelial cell" in the present invention means an epithelial cell present on the outside of the neural retinal tissue in retina in vivo. Whether it is a retinal pigment epithelial cell can be confirmed by those of ordinary skill in the art based on, for example, expression of a cell marker (RPE65 (matured retinal pigment epithelial cell), Mitf (juvenile or matured retinal pigment epithelial cell) and the like), the presence of melanin granule, characteristic cell morphology of polygon and the like.

First, in step (C), a cell aggregate containing a retinal tissue obtained by the production method 2 of the present invention is cultured in suspension in a serum-free medium or serum-containing medium free of a BMP signal transduction pathway activating substance but containing a Wnt signal transduction pathway activating substance to give an aggregate containing retinal pigment epithelial cells.

As a serum-free medium to be used in step (C), a serum-free medium which is a basal medium supplemented with N2 or KSR can be mentioned. More specifically, a serum-free medium which is a DMEM/F-12 medium supplemented with N2 supplement (Life Technologies) can be mentioned. As the serum-containing medium, a serum-containing medium which is a basal medium supplemented with fetal bovine serum can be mentioned.

The serum-free medium to be used in step (C) may contain, in addition to the aforementioned Wnt signal transduction pathway activating substance, the aforementioned Nodal/Activin signal transduction pathway activating substance, and/or the aforementioned FGF signal transduction pathway inhibiting substance.

A preferable culturing in step (C) is, for example, suspension culturing.

Step (D) in which the aggregate obtained in step (C) is dispersed and the obtained cells are cultured in and adhered state is explained.

Step (D) is performed within 60 days, preferably within 30 days, more preferably 3 days, after the start of step (C).

As a serum-free medium or serum-containing medium to be used for adhesion culturing in step (D), the aforementioned medium can be mentioned. To avoid complicated preparation, a serum-free medium supplemented with an appropriate amount of a commercially available serum alternative such as KSR and the like (e.g., a medium of 1:1 mixture of DMEM/F-12 and Neurobasal supplemented with ½×N2 supplement, ½×B27 supplement and 100 μM 2-mercaptoethanol) is preferably used. The amount of KSR to be added to the serum-free medium is, for example, generally about 1% to about 20%, preferably about 2% to about 20%, in the case of a cell derived from human iPS cell.

In step (D), it is preferable to culture cells in the aforementioned serum-free medium or serum-containing medium containing a ROCK inhibiting substance.

In step (D), it is more preferable to culture cells in a serum-free medium or serum-containing medium further containing one or more substances selected from the group consisting of a Wnt signal transduction pathway activating substance, a FGF signal transduction pathway inhibiting substance, an Activin signal transduction pathway activating substance and a BMP signal transduction pathway activating substance.

The Activin signal transduction pathway activating substance is a substance capable of enhancing a signal mediated by Activin. Examples of the Activin signal transduction pathway activating substance include proteins belonging to the Activin family (e.g., Activin A, Activin B, Activin C, Activin AB and the like), Activin receptor, and Activin receptor agonist.

The concentration of the Activin signal transduction pathway activating substance to be used in step (D) may be any as long as a uniformed sheet of retinal pigment epithelial cells can be efficiently formed. For example, Recombinant Human/Mouse/Rat Activin A (R&D systems, #338-AC) is added to a concentration of about 1 ng/ml to about 10 μg/ml, preferably about 10 ng/ml to about 1 μg/ml, more preferably about 100 ng/ml.

An Activin signal transduction pathway activating substance is added, for example, within 18 days, preferably on day 6, from the start of step (D).

In step (D), adhesion culturing is preferably performed on a culture vessel whose surface is treated with a culture substrate. As a culture substrate to be used for treating culture vessel in step (D), a cell culture substrate enabling adhesion culturing of aggregate-derived cells and formation of a retinal pigment epithelial sheet can be mentioned.

3. Method for Evaluating Toxicity or Efficacy

Since a retinal tissue or retinal cells (e.g., photoreceptor cell, retinal progenitor cell, retinal layer-specific neuron) produced by the production method of the present invention is useful as a material for disease study or drug discovery in a screening for a medicament for treating a disease due to a disorder of a retinal tissue or retinal cells, or in toxicity evaluation, it can be used as a reagent for evaluating toxicity or efficacy of a test substance. For example, iPS cells are produced from a human patient with a disease due to a disorder of a retinal tissue, particularly a hereditary disease, and using the iPS cells, a retinal tissue or retinal cells (e.g., photoreceptor cell, retinal progenitor cell, retinal layer-specific neuron) is produced by the method of the present invention. The retinal tissue or retinal cells may reproduce the disorder of retinal tissue causing the disease of the patient in vitro. Therefore, the present invention provides a method for evaluating toxicity or efficacy of a test substance, which comprises contacting the test substance with a retinal tissue or retinal cells (e.g., photoreceptor cell, retinal progenitor cell, retinal layer-specific neuron) produced by the production method of the present invention, and detecting an influence of the substance on the cells or tissue.

For example, a retinal tissue or retinal cells (e.g., photoreceptor cell, retinal progenitor cell, retinal layer-specific neuron) having a particular disorder (e.g., hereditary disorder), which is produced by the production method of the present invention, are cultured in the presence or absence (negative control) of a test substance. Then, the severity of disorder of the retinal tissue or retinal cells treated with the test substance is compared with that of the negative control. As a result, a test substance that reduced the severity of the disorder can be selected as a candidate substance for a medicament for treating the disease resulting from the disorder. For example, a test substance that improves the physiological activity (e.g., survival promotion or maturation) of retinal cells produced by the production method of the present invention can be searched for as a candidate substance of a pharmaceutical product. Alternatively, according to the production method of the present invention, retinal cells are prepared by inducing differentiation of the induced pluripotent stem cells which are prepared from a somatic cell having a gene mutation that causes a particular disorder such as a disease accompanied by a disorder in retina and the like.

A candidate of a test substance effective as a therapeutic drug or prophylactic drug for the disorder can be searched for based on whether the retinal cells added with a test substance show the aforementioned disorder, as an index.

For toxicity evaluation, a retinal tissue or retinal cells (e.g., photoreceptor cell, retinal progenitor cell, retinal layer-specific neuron) produced by the production method of the present invention are cultured in the presence or absence (negative control) of a test substance. Then, the severity of toxicity on the retinal tissue or retinal cells treated with the test substance is compared with that of the negative control. As a result, a test substance that exerted toxicity as compared to the negative control can be judged as a substance having toxicity to the retinal tissue or retinal cells (e.g., photoreceptor cell, retinal progenitor cell, retinal layer-specific neuron).

That is, the present invention encompasses a method for evaluating toxicity comprising the following steps:

(step 1) a step of culturing a retinal tissue or retinal cells produced by the production method of the present invention under viable culture conditions for a given time in the presence of a test substance, and measuring the severity of cell injury, (step 2) a step of culturing a retinal tissue or retinal cells produced by the production method of the present invention under viable culture conditions for a given time in the absence of test substance or in the presence of a positive control, and measuring the severity of cell injury, (step 3) a step of evaluating the toxicity of the test substance in step 1, based on the difference in the results measured in (step 1) and (step 2).

As used herein, "in the absence of a test substance" encompasses adding only a culture medium or a solvent used to dissolve the test substance instead of adding a test substance. In addition, "positive control" means a known compound having toxicity.

Examples of the method for measuring the severity of cell injury include a method for measuring the number of viable cells, for example, a method for measuring intracellular ATP amount, a method for measuring the number of viable cells by cell staining (e.g., nucleus staining) and morphology observation and the like.

In step 3, as a method for evaluating the toxicity of a test substance, the measurement value in step 1 and the measurement value of the negative control in step 2 are compared, and when the severity of cell injury in step 1 is high, the test substance can be judged to have toxicity. In addition, the measurement value in step 1 and the measurement value of the positive control in step 2 are compared, and when the severity of cell injury in step 1 is the same or above, the test substance can be judged to have toxicity.

4. Pharmaceutical Composition

The present invention provides a pharmaceutical composition containing an effective amount of a retinal tissue or retinal cells (e.g., photoreceptor cell, retinal progenitor cell, retinal layer-specific neuron) produced by the production method of the present invention.

The pharmaceutical composition contains an effective amount of a retinal tissue or retinal cells (e.g., photoreceptor cell, retinal progenitor cell, retinal layer-specific neuron) produced by the production method of the present invention, and a pharmaceutically acceptable carrier.

As a pharmaceutically acceptable carrier, a physiological aqueous solvent (saline, buffer, serum-free medium etc.) can be used. Where necessary, in a transplantation therapy, a medicament containing a tissue or cells to be transplanted may contain conventionally used preservative, stabilizer, reducing agent, isotonizing agent and the like.

The pharmaceutical composition of the present invention can be produced as a suspension by suspending retinal tissues or retinal cells produced by the production method 1 or 2 of the present invention in an appropriate physiological aqueous solvent. Where necessary, the composition may be added with a cryopreservative, cryopreserved, thawed when in use, washed with buffer, and used for a transplantation therapy.

A retinal tissue obtained by the production method of the present invention may also be cut in an appropriate size with tweezers and the like to give a sheet preparation.

Cells obtained by the production method of the present invention may also be subjected to adhesion culturing in step (3) for differentiation induction to form a sheet-like cells to give a sheet preparation.

The pharmaceutical composition of the present invention is useful as a therapeutic drug for a disease due to a disorder of a neural tissue or neural cells (e.g., retinal tissue, retinal progenitor cell, retinal layer-specific neuron).

5. Therapeutic Drug

A retinal tissue or retinal cells (e.g., photoreceptor cell, retinal progenitor cell, retinal layer-specific neuron) produced by the production method of the present invention is useful for a transplantation therapy for a disease due to a disorder of a retinal tissue or retinal cells. Thus, the present invention provides a medicament for treating a disease due to a disorder of a retinal tissue or retinal cells, which contains a retinal tissue or retinal cells (e.g., photoreceptor cell, retinal progenitor cell, retinal layer-specific neuron) produced by the production method of the present invention. A retinal tissue or retinal cells (including retinal progenitor cell, retinal layer-specific neuron) produced by the production method of the present invention can be used as a medicament for treating the disease due to a disorder of a retinal tissue or retinal cells or to complement the corresponding damaged site in a damaged state of a retinal tissue. A disease due to a disorder of a retinal tissue or retinal cells, and a damaged state of a retinal tissue can be treated by transplanting a retinal tissue or retinal cells produced by the production method of the present invention to a patient with a disease due to a disorder of a retinal tissue or retinal cells, or a damaged state of a retinal tissue, who requires transplantation, to complement the retinal cells or disordered retinal tissue itself. Examples of the disease due to a disorder of a retinal tissue or retinal cells include retinal denaturation, pigmentary degeneration of the retina, age-related macular degeneration, organic mercury poisoning, chloroquine retinopathy, glaucoma, diabetic retinopathy, retinopathy of newborn babies, and the like.

In transplantation therapy, rejection due to the difference in histocompatibility antigens often poses a problem. However, the problem can be solved by using pluripotent stem cells (e.g., induced pluripotent stem cells) established from the somatic cells of the transplantation recipient. That is, in a preferable embodiment, pluripotent stem cells (e.g., induced pluripotent stem cells) established from the somatic cells of the recipient are used as pluripotent stem cells in the method of the present invention, and a neural tissue or neural cells, which is immunologically self for the recipient, are produced and transplanted to the recipient.

In addition, an allogenic neural tissue or neural cell may be produced from a pluripotent stem cell (e.g., induced pluripotent stem cell) established from a somatic cell of others who are immunologically compatible with the recipient (e.g., compatible in HLA type and MHC type), and transplanted to the recipient.

EXAMPLES

The present invention is explained in detail in the following by referring to Examples and Pharmacological Examples, Examples, which are not to be construed as limitative.

Comparative Example 1: Example of Differentiation from Human iPS Cells without Using a Shh Signal Transduction Pathway Activating Substance in Step 2

Human iPS cells (1231A3 strain, obtained from Kyoto University) were cultured under feeder-free conditions according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

As a specific maintenance culture operation, subconfluent human iPS cells (1231A3 strain) were first washed with PBS, and dispersed into single cells by using TrypLE Select (manufactured by Life Technologies). Thereafter, the aforementioned human iPS cells dispersed into single cells were seeded in a plastic culture dish coated with Laminin 511-E8, and feeder-free culturing was performed in StemFit medium in the presence of Y27632 (ROCK inhibiting substance, 10 μM). When a 6-well plate (manufactured by Iwaki, for cell culture, culture area 9.4 cm$^2$) was used as the aforementioned plastic culture dish, the number of plated cells for the aforementioned human iPS cells dispersed into single cells was adjusted to $6 \times 10^3$. One day after seeding, the entire amount of the medium was changed with StemFit medium free of Y27632. Thereafter, once in 1-2 days, the entire amount of the medium was changed with StemFit medium free of Y27632. Thereafter, 6 days after seeding, the cells were cultured until subconfluent (60% of culture area is covered with cells).

The above subconfluent human iPS cells were treated with a cell dispersion solution by using TrypLE Select (Life Technologies), and further dispersed into single cells by a pipetting operation. Thereafter, the above human iPS cells dispersed into single cells were suspended in 100 μl of a serum-free medium in a non-cell-adhesive 96 well culture plate (PrimeSurface 96V-bottom plate, SUMITOMO BAKELITE) at $1.2 \times 10^4$ cells per well, and subjected to suspension culturing at 37° C., 5% $CO_2$. As a serum-free medium (gfCDM+KSR) therefor, a 1:1 mixture of F-12 medium and IMDM medium supplemented with 10% KSR, 450 μM 1-monothioglycerol, 1× Chemically defined lipid concentrate was used. At the start of the suspension culturing (on day 0 after the start of suspension culturing, step 2 start), Y27632 (final concentration 20 μM) was added to the above serum-free medium. By day 2 after the start of suspension culturing, cell aggregates were formed (step 2 completed, and step 3 start). On day 3 after the start of suspension culturing, a serum-free medium (50 μl) free of Y27632 was added.

On day 6 after the start of suspension culturing, a half amount of the medium was changed with a medium free of Y27632 and containing or not containing human recombinant BMP4 (manufactured by R&D) to adjust the final concentration of exogenous human recombinant BMP4 to 1.5 nM (55 ng/ml, FIG. 1B) or to give a medium free of exogenous human recombinant BMP4 (FIG. 1A). As the half-medium exchange operation, a half volume of the medium in the culture vessel, namely 75 μl, was discarded, the above fresh serum-free medium (75 μl) was added to adjust the total medium amount to 150 μl. Thereafter, a half amount of the medium was changed with the above serum-free medium free of Y27632 and human recombinant BMP4 once per 2-4 days. The thus-prepared cell aggregates were subjected to bright field observation under an inverted microscope (BIOREVO manufactured by KEYENCE) on day 19 after the start of suspension culturing (FIG. 1A, B). As a result, it was found that, both under conditions involving addition of human recombinant BMP4 (FIG. 1B), and conditions not involving addition (FIG. 1A), not less than 90% of cell aggregates were collapsed, and the neural tissue formation efficiency was poor.

Example 1: Example of Formation of Cell Aggregate, Neural Tissue and Retinal Tissue Prepared from Human iPS Cells Cultured Using StemFit as Feeder-Free Medium in Step 1, by Using a Shh Transduction Pathway Activating Substance in Step 2

Human iPS cells (1231A3 strain, obtained from Kyoto University) were cultured under feeder-free conditions according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used. The maintenance culturing was performed according to the method described in Comparative Example 1.

The thus-prepared subconfluent human iPS cells were treated with a cell dispersion solution by using TrypLE Select (Life Technologies), and further dispersed into single cells by a pipetting operation. Thereafter, the above human iPS cells dispersed into single cells were suspended in 100 μl of a serum-free medium in a non-cell-adhesive 96 well culture plate (PrimeSurface 96V-bottom plate, SUMITOMO BAKELITE) at $1.2 \times 10^4$ cells per well, and subjected to suspension culturing at 37° C., 5% $CO_2$. As a serum-free medium (gfCDM+KSR) therefor, a 1:1 mixture of F-12 medium and IMDM medium supplemented with 10% KSR, 450 μM 1-monothioglycerol, 1× Chemically defined lipid concentrate was used. At the start of the suspension culturing (on day 0 after the start of suspension culturing, step 2 start), Y27632 (final concentration 20 μM) and SAG (300 nM) as a Shh signal transduction pathway activating substance were added to the above serum-free medium. By day 2 after the start of suspension culturing, cell aggregates were formed (step 2 completed, step 3 start). On day 3 after the start of suspension culturing, a serum-free medium (50 μl) free of Y27632 and SAG was added. On day 6 after the start of suspension culturing, a half amount of the medium was changed with a medium free of Y27632 and containing or not containing human recombinant BMP4 (manufactured by R&D) to adjust the final concentration of exogenous human recombinant BMP4 to 1.5 nM (55 ng/ml, FIG. 1D) or to give a medium free of exogenous human recombinant BMP4 (FIG. 1C). As the half-medium exchange operation, a half volume of the medium in the culture vessel, namely 75 μl, was discarded, the above fresh serum-free medium (75 μl) was added to adjust the total medium amount to 150 μl. Thereafter, a half amount of the medium was changed with the above serum-free medium free of Y27632, SAG and human recombinant BMP4 once per 2-4 days. The thus-prepared cell aggregates were subjected to bright field observation under an inverted microscope (BIOREVO manufactured by KEYENCE) on day 19 after the start of suspension culturing (FIG. 1C, D). As a result, both under conditions involving addition of human recombinant BMP4 (FIG. 1D), and conditions not involving addition thereof (FIG. 1C), the cell aggregates were maintained, and neuroepithelial structure was observed. That is, it was found that addition of a Shh signal transduction pathway activating substance affords a good shape of aggregate and improves neural tissue formation efficiency (FIG. 1A-D). From the results, it was found that, by addition of a Shh signal transduction pathway activating substance at the start of the suspension culturing in step 2, a neural tissue can be produced efficiently from human iPS cells subjected to feeder-free culturing.

Figure 2:
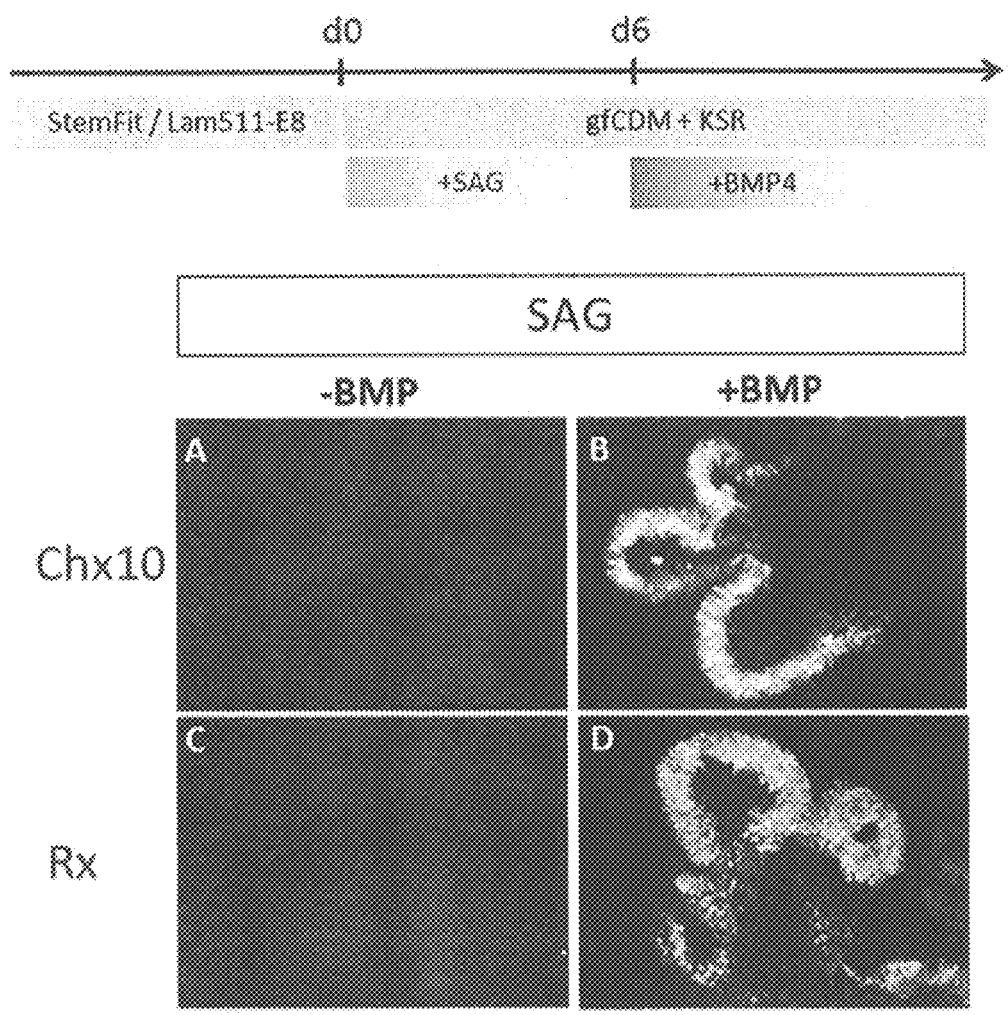
FIG. 2 shows culture conditions of Example 1, and immunohistochemical staining images of aggregates for retinal tissue markers (Chx10, Rx) (A-D).

The above cell aggregates on day 19 after the start of suspension culturing were each fixed with 4% para-formaldehyde to give cryosections. These cryosections were immunostained for Chx10 (anti-Chx10 antibody, manufactured by Exalpha, sheep), which is one of the retinal tissue markers, or Rx (anti-Rx antibody, manufactured by TAKARA, guinea pig), which is one of the retinal tissue markers. In judgment of whether the above marker is positive in the immunostaining analysis, a fluorescence intensity which is not less than 2 times higher than that of the background was taken as positive. As a result, it was found that, under conditions involving addition of a Shh signal transduction pathway activating substance on day 0 of suspension culturing and no addition of a BMP signal transduction pathway activating substance on day 6 of suspension culturing, the proportion of Rx-positive cells in the total cells was less than 3%, and the proportion of Chx10-positive cells was also less than 3% (FIG. 2A, C). On the other hand, it was found that, under conditions involving addition of a Shh signal transduction pathway activating substance on day 0 of suspension culturing and addition of a BMP signal transduction pathway activating substance on day 6 of suspension culturing, the proportion of Rx-positive cells in the total cells was not less than 60%, and the proportion of Chx10-positive cells was also not less than 60% (FIG. 2B, D). Furthermore, from the analysis of continuous sections, it was suggested that, in a neural tissue having a high (not less than 95%) proportion of Chx10- positive cells, Rx is also strongly positive (FIG. 2B, D). From these results, it was found that a retinal tissue can be efficiently produced from feeder-free-cultured human iPS cells (hereinafter sometimes to be referred to as feeder-free human iPS cells), by adding a Shh signal transduction pathway activating substance at the start of the suspension culturing in step 2 and adding a BMP signal transduction pathway activating substance as a differentiation induction substance during the suspension culturing in step 3.

Example 2: Example of Production of Neural Tissue from Human iPS Cells Using Essential 8 as a Feeder-Free Medium in Step 1, and Using a Shh Transduction Pathway Activating Substance at the Start of Suspension Culturing Human iPS cells (1231A3 strain, obtained from Kyoto University) were cultured under feeder-free conditions according to the method described in "Scientific Reports, 4, 3594 (2014)". As a feeder-free medium, Essential 8 medium (manufactured by Life Technologies) was used, and as a feeder-free scaffold, Laminin 511-E8 (manufactured by Nippi, Inc.) was used.

As a specific maintenance culture operation, the subconfluent human iPS cells (1231A3 strain) were first washed with PBS, and dispersed into single cells by using TrypLE Select (manufactured by Life Technologies). Thereafter, the above human iPS cells dispersed into single cells were seeded in a plastic culture dish coated with Laminin 511-E8, and subjected to feeder-free culturing in Essential 8 medium in the presence of Y27632 (ROCK inhibiting substance, 10 μM). When a 6-well plate (manufactured by Iwaki, for cell culture, culture area 9.4 cm$^2$) was used as the above plastic culture dish, the number of plated cells for the above human iPS cells dispersed into single cells was adjusted to 6×10$^3$. One day after seeding, the entire amount of the medium was changed with Essential 8 medium free of Y27632. Thereafter, once in 1-2 days, the entire amount of the medium was changed with Essential 8 medium free of Y27632. Thereafter, the cells were cultured until subconfluence (60% of culture area is covered with cells) 6 days after seeding.

Figure 3:
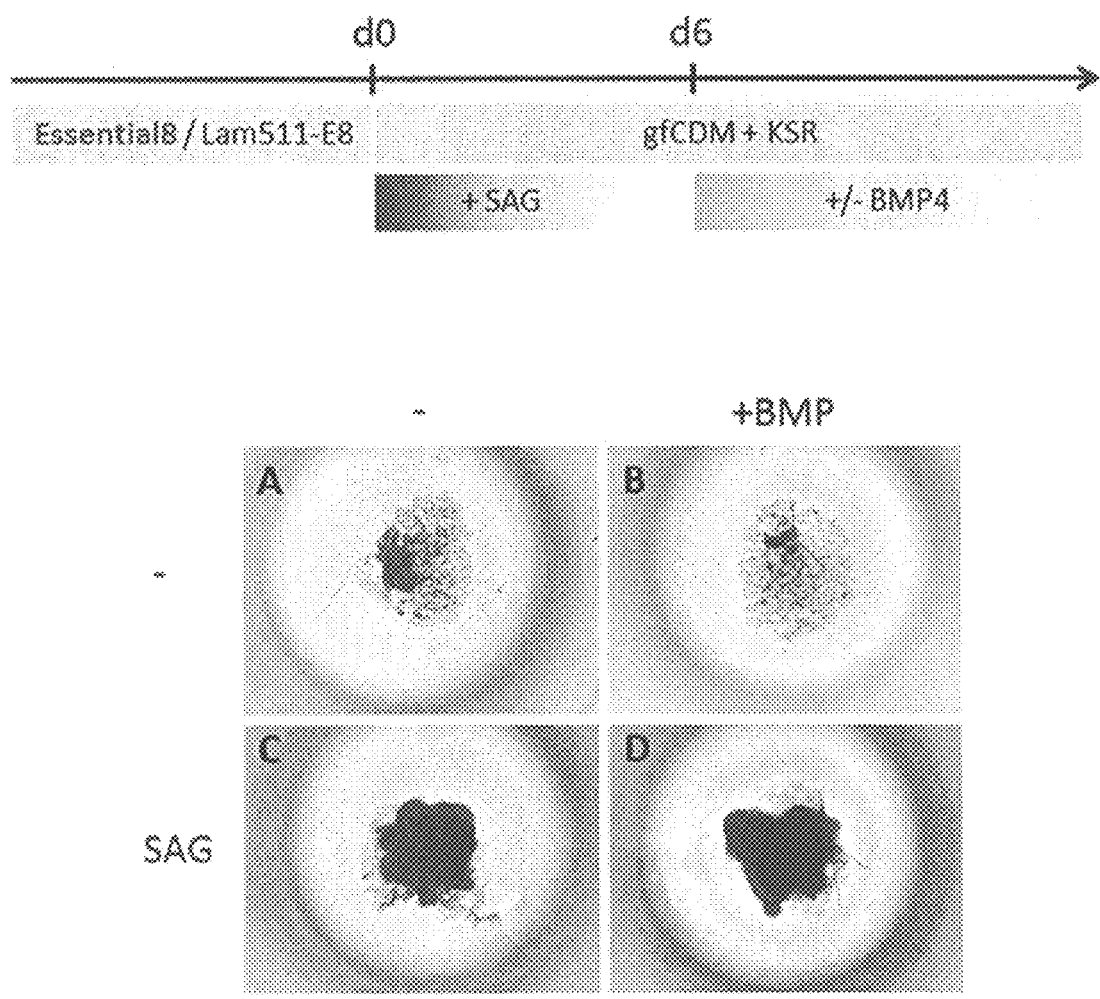
FIG. 3 shows culture conditions of Example 2 and bright field images of aggregates (A-D).

The thus-prepared subconfluent human iPS cells were treated with the cell dispersion solution by using TrypLE Select (Life Technologies), further dispersed into single cells by pipetting operation, and the above human iPS cells dispersed into single cells were suspended in 100 μl of a serum-free medium at 1.2×10$^4$ cells per well of a non-cell-adhesive 96-well culture plate (PrimeSurface 96V-bottom plate, manufactured by SUMITOMO BAKELITE). Thereafter, the cells were subjected to suspension culturing at 37° C., 5% CO$_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), a serum-free medium supplemented with Y27632 (final concentration 20 μM) was used (FIG. 3A-D). Of these, under certain conditions, a serum-free medium supplemented with Y27632 (final concentration 20 μM) and SAG (300 nM) as a Shh signal transduction pathway activating substance was used (FIG. 3C, D). By day 2 after the start of suspension culturing, cell aggregates were formed under both conditions with and without addition of SAG (step 2 completed, step 3 start). On day 3 after the start of suspension culturing, a serum-free medium (50 μl) free of Y27632 and SAG was added. On day 6 after the start of suspension culturing, a half amount of the medium was changed with a medium free of Y2763 and SAG and containing or not containing human recombinant BMP4 (manufactured by R&D) to set the final concentration of exogenous human recombinant BMP4 to 1.5 nM (FIG. 3B, D) or to give a medium free of exogenous human recombinant BMP4 (FIG. 3A, C). Thereafter, a half amount of the medium was changed with the above serum-free medium free of Y27632, SAG and human recombinant BMP4 once per 2-4 days. The thus-prepared cell aggregates on day 18 after the start of suspension culturing were subjected to bright field observation under an inverted microscope (BIOREVO manufactured by KEYENCE) (FIG. 3A-D). As a result, it was found that not less than 80% of cell aggregates were collapsed, and formation efficiency of neural tissue was poor both of under conditions without addition of SAG at the start of the suspension culturing and without addition of BMP4 during suspension culturing (Condition 1, FIG. 3A), and under conditions without addition of SAG at the start of the suspension culturing and with addition of BMP4 during suspension culturing (Condition 2, FIG. 3B). On the other hand, it was found that cell aggregates were maintained, and neuroepithelial structure was efficiently formed under conditions with addition of SAG at the start of the suspension culturing and without addition of BMP4 during suspension culturing (Condition 3, FIG. 3C), and under conditions with addition of SAG at the start of the suspension culturing and with addition of BMP4 during suspension culturing (Condition 4, FIG. 3D).

Figure 4:
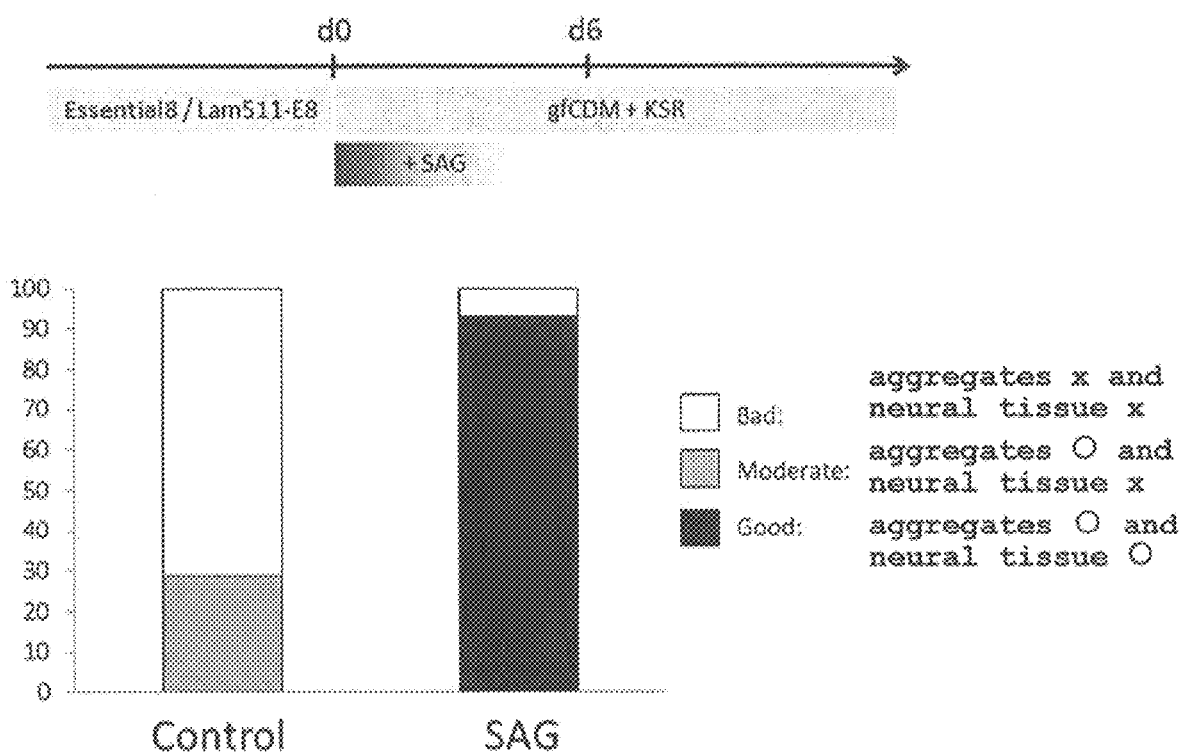
FIG. 4 shows culture conditions of Example 2 (no BMP4 treatment), and a graph quantifying the level of the morphology of aggregates.

Furthermore, forms of the plural aggregates were observed on day 18 after the start of suspension culturing, and categorized into good form (FIG. 4 black bar, good aggregates, containing many neuroepithelia), moderate level form (FIG. 4 gray bar, good aggregates but low proportion of neuroepithelium), and bad form (FIG. 4 white bar, aggregates collapsed, free of neuroepithelium) and quantified. As a result, under Condition 1 (FIG. 3A), the proportion of good form was less than 3%, and the proportion of bad form was 71% (FIG. 4, Control). In contrast, under Condition 3 (FIG. 3C), the proportion of good form was 93%, and the proportion of bad form was 6% (FIG. 4, SAG).

From these results, it was found that, with respect to feeder-free human iPS cells cultured in Essential 8 medium, efficiency of neural tissue formation is improved by adding Shh signal transduction pathway activating substance at the start of the suspension culturing.

Example 3: Example of Production of Retinal Tissue from Human iPS Cells by Using Essential 8 as Feeder-Free Medium in Step 1, and Using a Shh Transduction Pathway Activating Substance at the Start of Suspension Culturing Human iPS cells (201B7 strain, obtained from Kyoto University) were cultured under feeder-free according to the method described in "Scientific Reports, 4, 3594 (2014)". As a feeder-free medium, Essential 8 medium (manufactured by Life Technologies) was used, and as a feeder-free scaffold, Laminin 511-E8 (manufactured by Nippi, Inc.) was used.

As a specific maintenance culture operation, the subconfluent human iPS cells (201B7 strain) were first washed with PBS, and dispersed into single cells by using TrypLE Select (manufactured by Life Technologies). Thereafter, the above human iPS cells dispersed into single cells were seeded in a plastic culture dish coated with Laminin 511-E8, and subjected to feeder-free culturing in Essential 8 medium in the presence of Y2763 (ROCK inhibiting substance, 10 μM).

When a 6-well plate (manufactured by Iwaki, for cell culture, culture area 9.4 cm$^2$) was used as the above plastic culture dish, the number of plated cells for the above human iPS cells dispersed into single cells was adjusted to 6×10$^3$. One day after seeding, the entire amount of the medium was changed with Essential 8 medium free of Y27632. Thereafter, once in 1-2 days, the total amount of the medium was changed with Essential 8 medium free of Y27632. Thereafter, the cells were cultured until subconfluence (60% of culture area is covered with cells) 6 days after seeding.

The thus-prepared subconfluent human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at 1.2×10$^4$ cells per well of a non-cell-adhesive 96-well culture plate (PrimeSurface 96V-bottom plate, SUMITOMO BAKELITE). Thereafter, the cells were subjected to suspension culturing at 37° C., 5% CO$_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), a serum-free medium supplemented with SAG (final concentration 300 μM) as a Shh signal transduction pathway activating substance and Y27632 (20 μM) was used (FIG. 5A-D). By day 2 after the start of suspension culturing, cell aggregates were formed. On day 3 after the start of suspension culturing, a serum-free medium (50 μl) free of Y2763 and SAG was added. On day 6 after the start of suspension culturing, a half amount of the medium was changed with a medium free of Y2763 and SAG and containing or not containing human recombinant BMP4 (manufactured by R&D) to adjust the final concentration of exogenous human recombinant BMP4 to 1.5 nM (55 ng/ml). Thereafter, a half amount of the medium was changed with the above serum-free medium free of Y27632, SAG and human recombinant BMP4 once per 2-4 days. The thus-prepared cell aggregates were subjected to bright field observation under an inverted microscope (BIOREVO manufactured by KEYENCE) on day 18 after the start of suspension culturing. As a result, it was found that neuroepithelium was formed.

Figure 5:
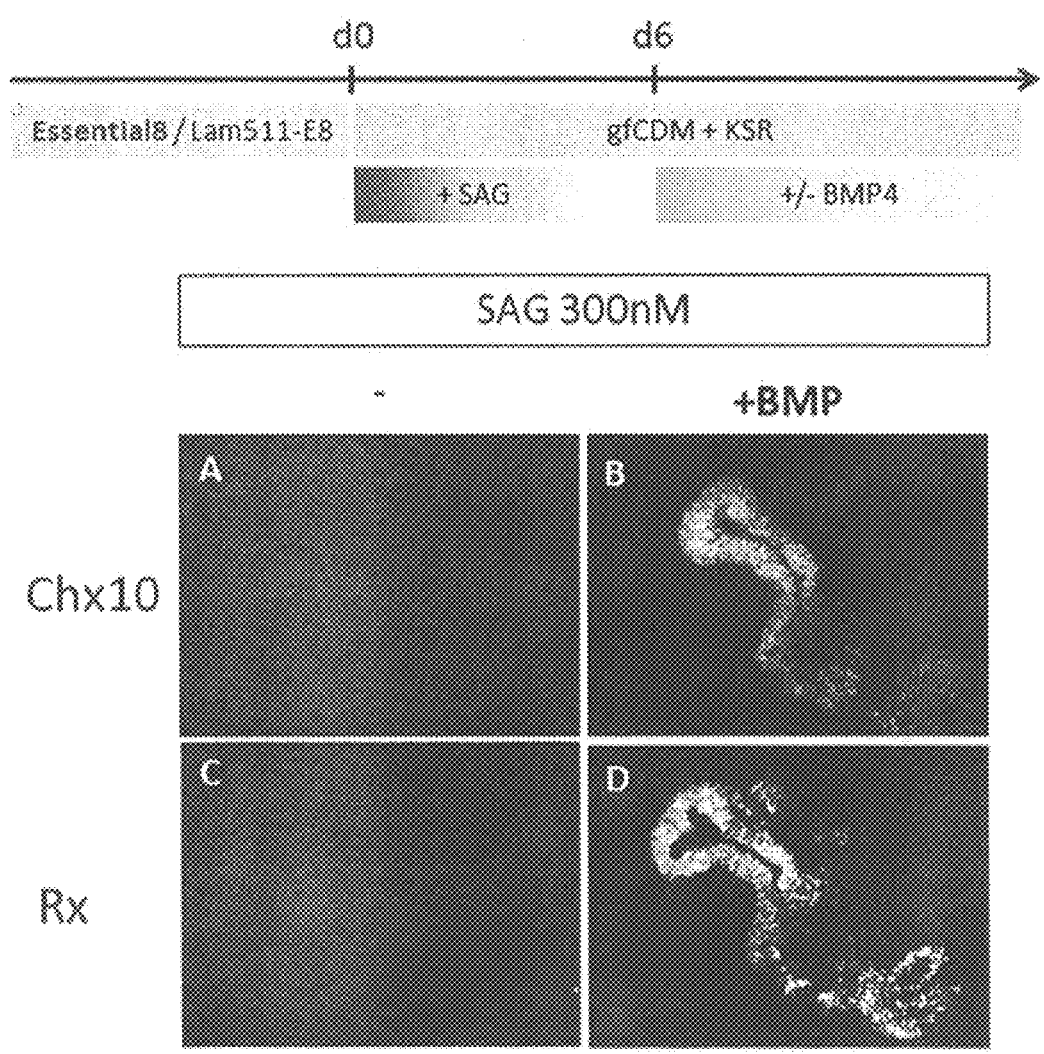
FIG. 5 shows culture conditions of Example 3, and immunohistochemical staining images of aggregates for retinal tissue markers (Chx10, Rx) (A-D).

Cell aggregates on day 18 after the start of suspension culturing were fixed with 4% para-formaldehyde to produce frozen sections. These frozen sections were immunostained for Chx10 (anti-Chx10 antibody, Exalpha, sheep), which is one of the retinal tissue markers, or Rx (anti-Rx antibody, manufactured by TAKARA, guinea pig), which is one of the retinal tissue markers. As a result, it was found that, under conditions involving addition of a Shh signal transduction pathway activating substance on day 0 of suspension culturing and no addition of a BMP signal transduction pathway activating substance on day 6 of suspension culturing, the proportion of Rx-positive cells in the total cells was not more than 3%, and the proportion of Chx10-positive cells was also not more than 3% (FIG. 5A, C). On the other hand, it was found that, under conditions involving addition of a Shh signal transduction pathway activating substance on day 0 of suspension culturing and addition of a BMP signal transduction pathway activating substance on day 6 of suspension culturing, the proportion of Rx-positive cells in the total cells was not less than 40%, and the proportion of Chx10-positive cells was also not less than 40% (FIG. 5B, D). Furthermore, it was suggested from the analysis of serial sections that, in a neural tissue having a high (not less than 95%) proportion of Chx10-positive cells, Rx is also strongly positive (FIG. 5B, D). From these results, it was found that a retinal tissue can be efficiently produced from feeder-free human iPS cells, by the addition of a Shh signal transduction pathway activating substance at the start of the suspension culturing in step 2 and addition of a BMP signal transduction pathway activating substance as a differentiation induction substance during the suspension culturing in step 3.

Example 4: Example of Production of Retinal Tissue from Human iPS Cells by Using a Shh Transduction Pathway Activating Substance in Step 2, and Using BMP4 in Step 3

Human iPS cells (1231A3 strain, obtained from Kyoto University) were subjected to feeder-free culturing according to the method described in "Scientific Reports, 4, 3594 (2014)". As a feeder-free medium, StemFit medium (AK03, manufactured by Ajinomoto Co., Inc.) was used, and as a feeder-free scaffold, Laminin 511-E8 (manufactured by Nippi, Inc.) was used.

As a specific maintenance culture operation, subconfluent human iPS cells (1231A3 strain) were first washed with PBS, and dispersed into single cells by using TrypLE Select (manufactured by Life Technologies). Thereafter, the above human iPS cells dispersed into single cells were seeded in a plastic culture dish coated with Laminin 511-E8, and subjected to feeder-free culturing in StemFit medium in the presence of Y2763 (ROCK pathway inhibiting substance, 10 μM). When a 6-well plate (manufactured by Iwaki, for cell culture, culture area 9.4 cm$^2$) was used as the above plastic culture dish, the number of plated cells for the above human iPS cells dispersed into single cells was adjusted to 6×10$^3$. One day after seeding, the medium was changed with StemFit medium free of Y27632. Thereafter, once in 1-2 days, the medium was changed with StemFit medium free of Y27632. Thereafter, the cells were cultured until subconfluent (60% of culture area is covered with cells) 6 days after seeding.

The above subconfluent human iPS cells were dispersed into single cells by using TrypLE Select (Life Technologies), and the above human iPS cells dispersed into single cells were suspended in 100 μl of a serum-free medium at 1.2×10$^4$ cells per well of a non-cell-adhesive 96-well culture plate (PrimeSurface 96V-bottom plate, SUMITOMO BAKELITE), and subjected to suspension culturing at 37° C., 5% CO$_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), Y2763 (final concentration 20 μM) and SAG (final concentration 300 nM) were added to the above serum-free medium. By day 2 after the start of suspension culturing, cell aggregates were formed (step 2 completed, step 3 start).

Here, as step 3, culturing was performed under the following Condition 1 and Condition 2.

In Condition 1 (+BMP, d3), a medium (50 μl) free of Y2763 and SAG and containing human recombinant BMP4 (manufactured by R&D) was added on day 3 after the start of suspension culturing such that the final concentration of the exogenous human recombinant BMP4 was adjusted to 1.5 nM (total medium amount 150 μl). On day 6 after the start of suspension culturing, a half amount of the medium was changed with the above serum-free medium free of Y27632, SAG and human recombinant BMP4.

In Condition 2 (+BMP, d6), a serum-free medium (50 µl) free of Y27632, SAG and human recombinant BMP4 was added on day 3 after the start of suspension culturing. On day 6 after the start of suspension culturing, a half amount of the medium was changed with a medium free of Y2763 and SAG and containing human recombinant BMP4 (manufactured by R&D) such that the final concentration of the exogenous human recombinant BMP4 was adjusted to 1.5 nM.

On day 6 or later after the start of suspension culturing of the cells under Condition 1 and Condition 2, a half amount of the medium was changed with the above serum-free medium free of Y27632, SAG and human recombinant BMP4 once per 2-4 days. On day 18 after the start of suspension culturing, the form was observed under an inverted microscope. It was found that the cell aggregates were maintained, and a neural tissue was formed under Condition 1 and Condition 2.

Figure 6:
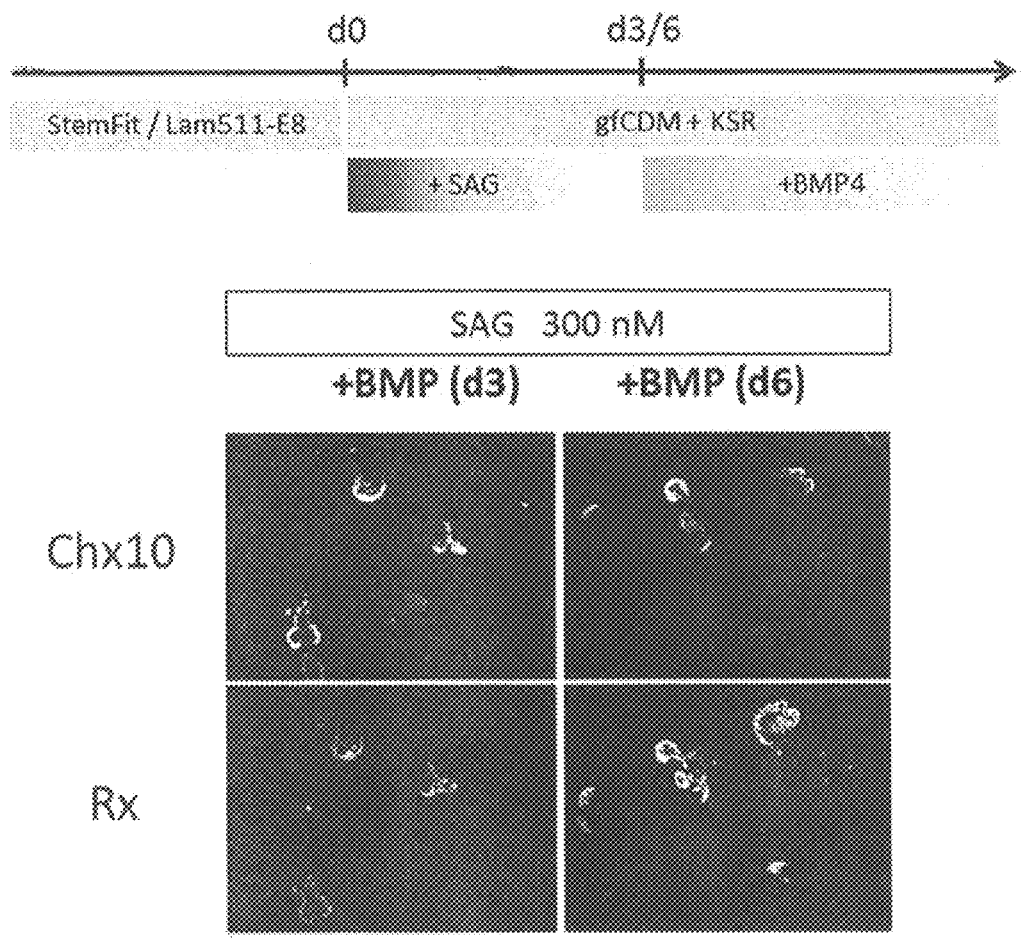
FIG. 6 shows immunostaining images of retinal tissues produced under culture conditions of Example 4 for retinal tissue markers.

The thus-prepared cell aggregates on day 18 after the start of suspension culturing, which were produced by adding SAG in step 2 from feeder-free iPS cells as a starting material, were fixed with 4% para-formaldehyde to produce frozen sections. These frozen sections were immunostained for Chx10 (anti-Chx10 antibody, Exalpha, sheep), which is one of the retinal tissue markers, or Rx (anti-Rx antibody, manufactured by TAKARA, guinea pig), which is one of the retinal tissue markers. These immunostained sections were observed under an inverted fluorescence microscope. As a result, it was found that the proportion of Rx-positive cells in the total cells was about 40%, and the proportion of Chx10-positive cells was also about 40%, for both the cells under Condition 1 and Condition 2 (FIG. 6). Furthermore, from the analysis of the serial sections, it was found that Rx is also strong positive in neural tissues having a high proportion of Chx10-positive cells (about 95%). From these results, it was found that a retinal tissue can be efficiently produced from feeder-free human iPS cells, by adding SAG in step 2 and adding a BMP signal transduction pathway activating substance as a differentiation induction substance during suspension culturing on day 3 or 6 after the start of suspension culturing in step 3.

Example 5: Example of Production of Retinal Tissue from Human iPS Cells by Using 600 nM Shh Transduction Pathway Activating Substance in Step 2, and Using BMP4 in Step 3

Feeder free human iPS cells (1231A3 strain) prepared according to the method described in Example 4 were dispersed into single cells by using TrypLE Select (Life Technologies), and the above human iPS cells dispersed into single cells were suspended in 100 µl of a serum-free medium at $1.2 \times 10^4$ cells per well of a non-cell-adhesive 96-well culture plate (PrimeSurface 96V-bottom plate, SUMITOMO BAKELITE), and subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 µM 1-monothioglycerol, 1× Chemically defined lipid concentrate was used. At the time of the start of suspension culturing (day 0 after the start of suspension culturing, start of step 2), Y2763 (final concentration 20 µM) and SAG (final concentration 600 nM) were added to the above serum-free medium. By day 2 after the start of suspension culturing, cell aggregates were formed (step 2 completed, step 3 start).

Here, as step 3, culturing was performed under the following Condition 1 and Condition 2.

In Condition 1 (+BMP, d3), a medium (50 µl) free of Y2763 and SAG and containing human recombinant BMP4 (manufactured by R&D) was added on day 3 after the start of suspension culturing such that the final concentration of the exogenous human recombinant BMP4 was adjusted to 1.5 nM (total medium amount 150 µl). On day 6 after the start of suspension culturing, a half amount of the medium was changed with the above serum-free medium free of Y27632, SAG and human recombinant BMP4.

In Condition 2 (+BMP, d6), a serum-free medium (50 µl) free of Y27632, SAG and human recombinant BMP4 was added on day 3 after the start of suspension culturing. On day 6 after the start of suspension culturing, a half amount of the medium was changed with a medium free of Y2763 and containing human recombinant BMP4 (manufactured by R&D) such that the final concentration of the exogenous human recombinant BMP4 was adjusted to 1.5 nM.

On day 6 or later after the start of suspension culturing of the cells under Condition 1 and Condition 2, a half amount of the medium was changed with the above serum-free medium free of Y27632, SAG and human recombinant BMP4 once per 2-4 days. On day 18 after the start of suspension culturing, the form was observed under an inverted microscope. It was found that the cell aggregates were maintained, and a neural tissue was formed under Condition 1 and Condition 2.

Figure 7:
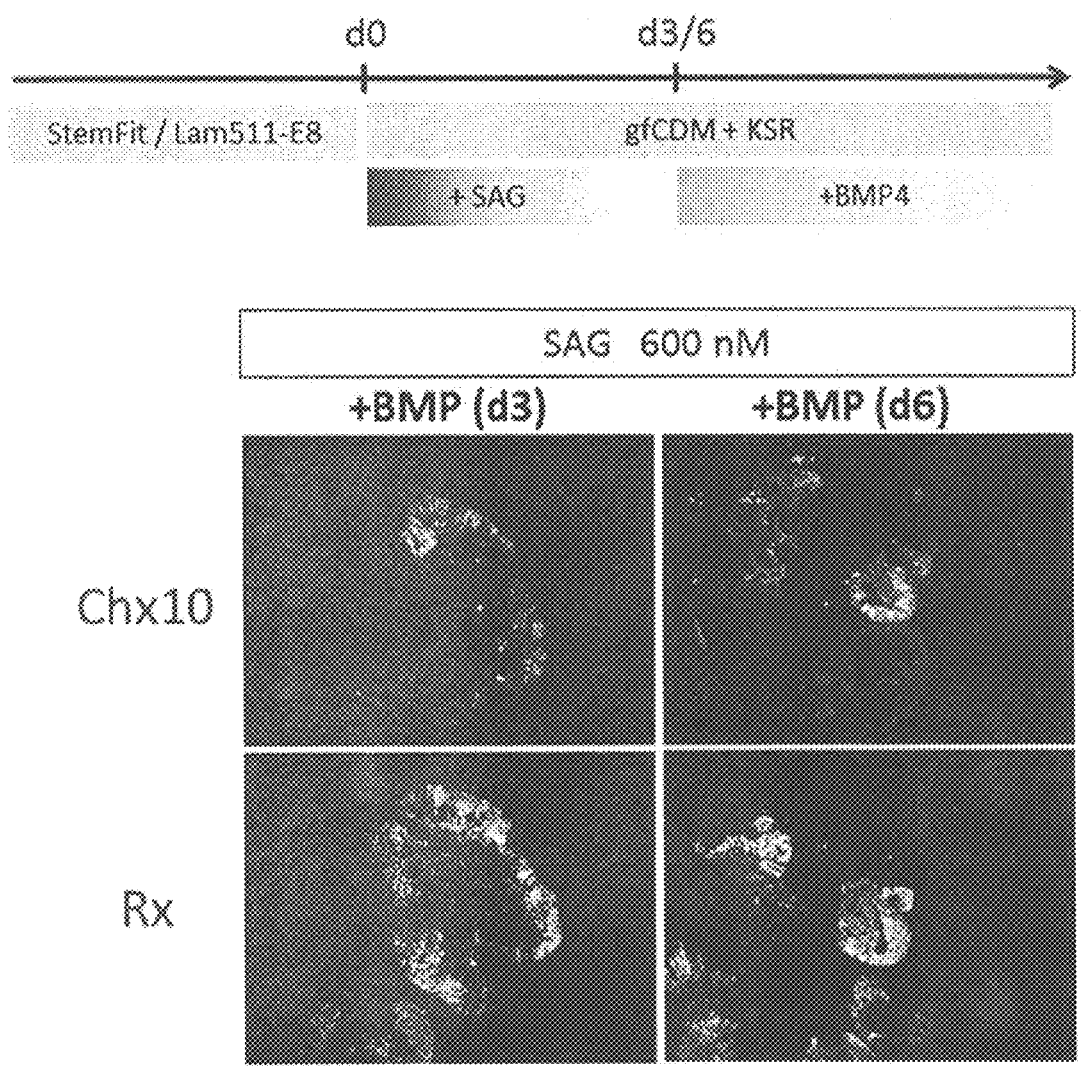
FIG. 7 shows immunostaining images of retinal tissues produced under culture conditions of Example 5 for retinal tissue markers.

The thus-prepared cell aggregates on day 18 after the start of suspension culturing, which were produced by adding SAG in step 2 from feeder-free iPS cells as a starting material, were fixed with 4% para-formaldehyde to produce frozen sections. These frozen sections were immunostained for Chx10 (anti-Chx10 antibody, Exalpha, sheep), which is one of the retinal tissue markers, or Rx (anti-Rx antibody, manufactured by TAKARA, guinea pig), which is one of the retinal tissue markers. These immunostained sections were observed under an inverted fluorescence microscope. As a result, it was found that the proportion of Rx-positive cells in the total cells was about 40%, and the proportion of Chx10-positive cells was also about 40%, for both the cells under Condition 1 and Condition 2 (FIG. 7). Furthermore, from the analysis of the continuous sections, it was suggested that Rx is also strong positive in neural tissues having a high proportion of Chx10-positive cells (about 95%). From the results, it was found that a retinal tissue can be efficiently produced from feeder-free human iPS cells, by adding 600 nM SAG in step 2 and adding a BMP signal transduction pathway activating substance as a differentiation induction substance on day 3 or 6 after the start of suspension culturing in step 3.

Example 6: Example of Production of Retinal Tissue from Human iPS Cells by Using SAG, Purmorphamine, or Recombinant Shh Protein as a Sonic Hedgehog Signal Transduction Pathway Activating Substance in Step 2

Human iPS cells (201B7 strain, obtained from Kyoto University) were cultured under feeder-free according to the method described in "Scientific Reports, 4, 3594 (2014)". As a feeder-free medium, Stem Fit medium (AK-03; manufactured by Ajinomoto Co., Inc.) was used, and as a feeder-free scaffold, Laminin 511-E8 (manufactured by Nippi, Inc.) was used.

As a specific maintenance culture operation, the subconfluent human iPS cells (201B7 strain) were first washed with PBS, and dispersed into single cells by using TrypLE Select (manufactured by Life Technologies). Thereafter, the above human iPS cells dispersed into single cells were seeded in a plastic culture dish coated with Laminin 511-E8, and subjected to feeder-free culturing in Stem Fit medium in the presence of Y2763 (ROCK pathway inhibiting substance, 10 μM). When a 6-well plate (manufactured by Iwaki, for cell culture, culture area 9.4 cm$^2$) was used as the above plastic culture dish, the number of plated cells for the above human iPS cells dispersed into single cells was adjusted to 1.3×10$^4$. One day after seeding, the entire amount of the medium was changed with Stem Fit medium free of Y27632. Thereafter, once in 1-2 days, the entire amount of the medium was changed with Stem Fit medium free of Y27632. Thereafter, the cells were cultured until subconfluence (60% of culture area is covered with cells) 6 days after seeding.

Figure 8:
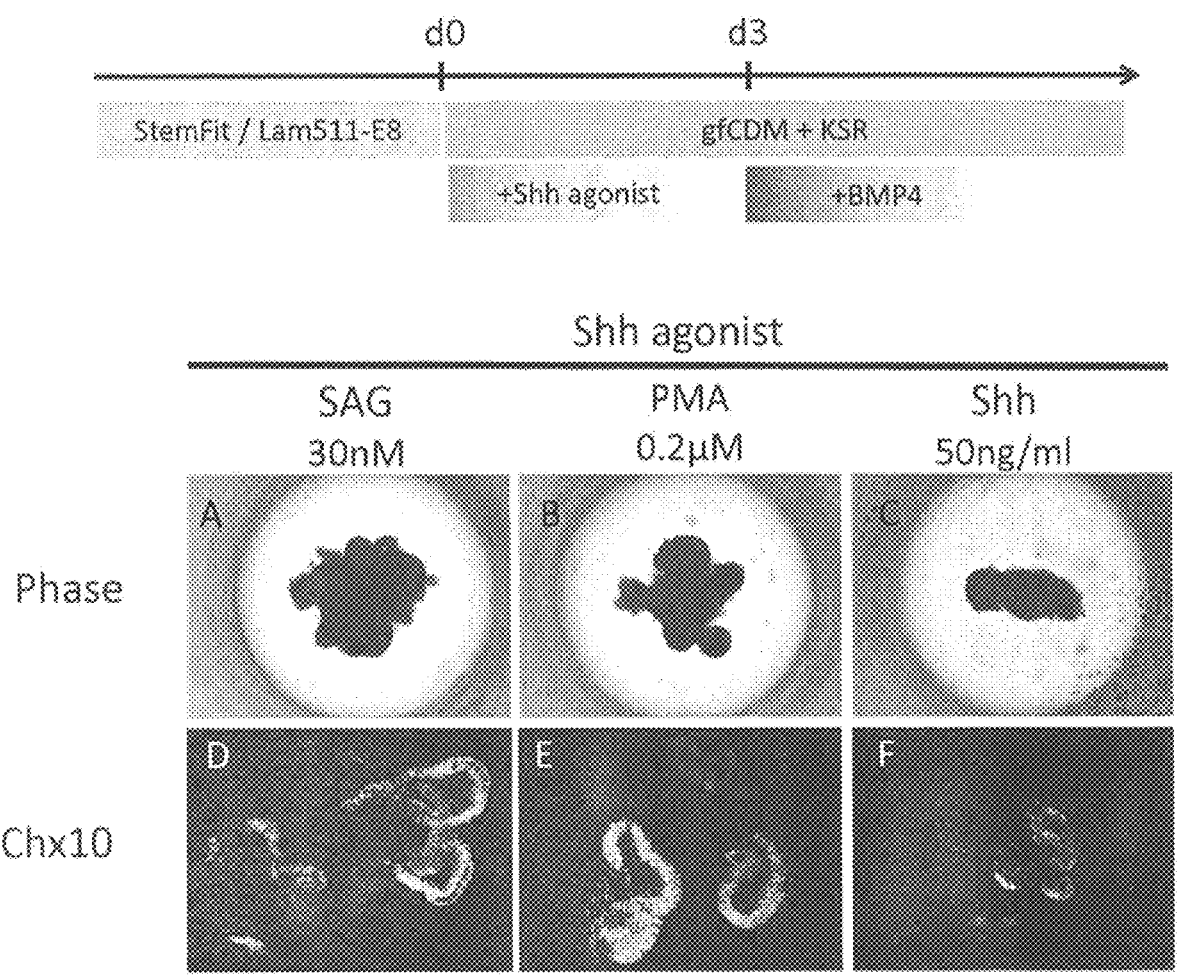
FIG. 8 shows bright field images of aggregates produced under culture conditions of Example 6 (A-C), and immunostaining images for retinal tissue marker (Chx10) (D-F).

The thus-prepared subconfluent human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at 1.0×10$^4$ cells per well of a non-cell-adhesive 96-well culture plate (SUMILON SPHEROID V-bottom plate PrimeSurface 96V-bottom plate, SUMITOMO BAKELITE). Thereafter, the cells were subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), the above serum-free medium supplemented with Y2763 (final concentration 20 μM) and further supplemented with SAG (final concentration 30 nM), Purmorphamine (manufactured by Wako, final concentration 0.2 μM), or human recombinant Shh (manufactured by R&D, Recombinant N-Terminus, final concentration 50 ng/ml) as a Shh signal transduction pathway activating substance was used (FIG. 8). On day 2 after the start of suspension culturing, a cell aggregates were formed. On day 3 after the start of suspension culturing, a medium (50 μl) free of Y27632, SAG, Purmorphamine and recombinant Shh and containing human recombinant BMP4 was added to adjust the final concentration of exogenous human recombinant BMP4 to 1.5 nM (55 ng/ml). On day 6 after the start of suspension culturing, a half amount of the medium was changed with a serum-free medium free of Y27632, SAG, Purmorphamine, recombinant Shh and human recombinant BMP4. Thereafter, a half amount of the medium was changed with the above serum-free medium free of Y27632, SAG and human recombinant BMP4 once per 2-4 days. The thus-prepared cell aggregates on day 18 after the start of suspension culturing were subjected to bright field observation under an inverted microscope (BIOREVO manufactured by KEYENCE). As a result, it was found that neuroepithelium was formed.

Cell aggregates on day 18 after the start of suspension culturing were fixed with 4% para-formaldehyde to produce frozen sections. These frozen sections were immunostained for Chx10 (anti-Chx10 antibody, Exalpha, sheep), which is one of the retinal tissue markers. As a result, it was found that, under conditions involving addition of SAG, PMA or Shh as a Shh signal transduction pathway activating substance on day 0 of suspension culturing, and addition of BMP4 on day 3 of suspension culturing, the proportion of Chx10-positive cells in the total cells was not more than 30% (FIG. 8, D-F). From these results, it was found that a retinal tissue can be efficiently produced from feeder-free cultured human iPS cells, by adding any of SAG Purmorphamine and recombinant Shh as a Shh signal transduction pathway activating substance at the start of the suspension culturing in step 2, and adding a BMP signal transduction pathway activating substance as a differentiation induction substance during the suspension culturing in step 3.

Example 7: Example of Production of Retinal Tissue from Human iPS Cells by Using SAG, Purmorphamine, or Recombinant Shh Protein as a Sonic Hedgehog Signal Transduction Pathway Activating Substance in Step 2 and Using BMP4 in Step 3

Human iPS cells (1231A3 strain, obtained from Kyoto University) were cultured under feeder-free according to the method described in "Scientific Reports, 4, 3594 (2014)". As a feeder-free medium, Stem Fit medium (AK-03; manufactured by Ajinomoto Co., Inc.) was used, and as a feeder-free scaffold, Laminin 511-E8 (manufactured by Nippi, Inc.) was used.

Figure 9:
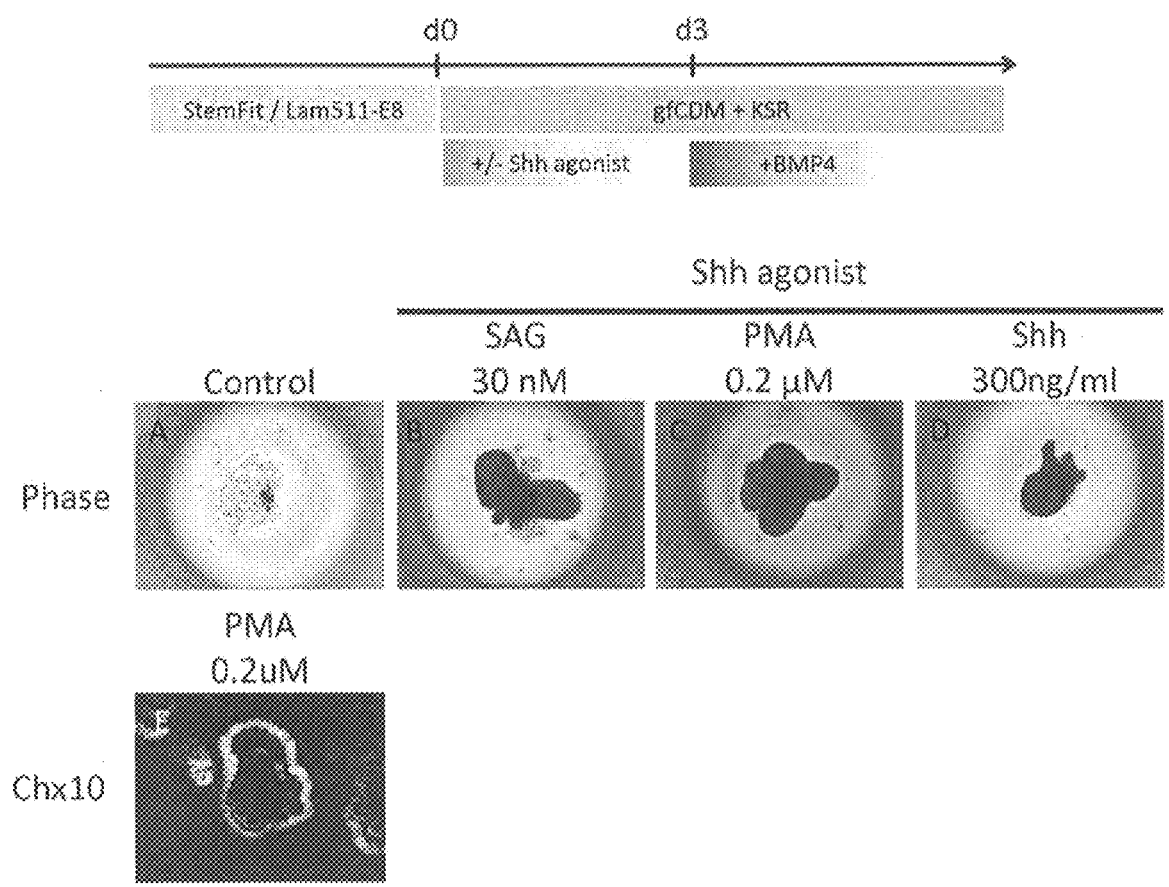
FIG. 9 shows bright field images of aggregates produced under culture conditions of Example 7 (A-D), and immunostaining image for retinal tissue marker (Chx10) (E).

The subconfluent human iPS cells prepared according to the method described in Example 6 were treated with the cell dispersion solution by using TrypLE Select (manufactured by Life Technologies), further dispersed into single cells by pipetting operation, and the above human iPS cells dispersed into single cells were suspended in 100 μl of a serum-free medium at 1.0×10$^4$ cells per well of a non-cell-adhesive 96-well culture plate (SUMILON SPHEROID V-bottom plate PrimeSurface 96V-bottom plate, SUMITOMO BAKELITE). Thereafter, the cells were subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), the above serum-free medium supplemented with Y2763 (final concentration 20 μM) and further supplemented with SAG (final concentration 30 nM), Purmorphamine (PMA, manufactured by Wako, final concentration 0.2 μM), or human recombinant Shh (manufactured by R&D, Recombinant N-Terminus, final concentration 300 ng/ml) as a Shh signal transduction pathway activating substance, or a serum-free medium free of a Shh signal transduction pathway activating substance was used (FIG. 9). On day 2 after the start of suspension culturing, cell aggregates were formed. On day 3 after the start of suspension culturing, a medium (50 μl) free of Y27632, SAG, Purmorphamine and Shh protein and containing human recombinant BMP4 (R&D) was added to adjust the final concentration of exogenous human recombinant BMP4 to 1.5 nM (55 ng/ml). On day 6 after the start of suspension culturing, a half amount of the medium was changed with a serum-free medium free of Y27632, SAG, Purmorphamine, Shh protein and human recombinant BMP4. Thereafter, a half amount of the medium was changed with the above serum-free medium free of Y27632, SAG, Purmorphamine, recombinant Shh and human recombinant BMP4 once per 2-4 days. The thus-prepared cell aggregates were subjected to bright field observation under an inverted microscope (BIOREVO manufactured by KEYENCE) on day 18 after the start of suspension culturing. As a result, it was found that cell aggregated did not grow and neuroepithelial was not formed under conditions without addition of an exogenous Shh signal transduction pathway activating substance in step 2 (FIG. 9: Control), whereas a cell aggregates grew and neuroepithelium was formed under conditions with addition of SAG, PMA or recombinant Shh protein in step 2 (FIG. 9: SAG, PMA, Shh).

The cell aggregates on day 18 after the start of suspension culturing were fixed with 4% para-formaldehyde to produce frozen sections. These frozen sections were immunostained for Chx10 (anti-Chx10 antibody, Exalpha, sheep), which is one of the retinal tissue markers. As a result, it was found that, under conditions involving addition of PMA on day 0 of suspension culturing, and addition of BMP4 on day 3 of suspension culturing, the proportion of Chx10-positive cells in the total cells was not more than 60% (FIG. 9 lower panel PMA). In addition, it was found that the cell aggregate contained Chx10-positive cells even under conditions with addition of SAG or Shh on day 0 of suspension culturing. From these results, it was found that a retinal tissue can be produced from feeder-free human iPS cells by adding any of SAG, Purmorphamine and recombinant Shh as a Shh signal transduction pathway activating substance at the start of the suspension culturing in step 2 and adding a BMP signal transduction pathway activating substance as a differentiation induction substance during the suspension culturing in step 3.

Example 8: Example of Production of Retinal Tissue by Subjecting Human iPS Cells Established Using Sendaivirus to Feeder-Free Culturing, Using a Shh Signal Transduction Pathway Activating Substance at the Start of the Suspension Culturing, and Using BMP4 in Step 3

Human iPS cells (DSPC-3 strain, established by Sumitomo Dainippon Pharma Co., Ltd.) were established using commercially available Sendaivirus vectors (4 factors of Oct3/4, Sox2, KLF4, c-Myc, CytoTune kit manufactured by DNAVEC (now ID Pharma)), StemFit medium (AK03; manufactured by Ajinomoto Co., Inc.), and Laminin 511-E8 (manufactured by Nippi, Inc.), and based on the methods described in published protocol of Life Technologies (iPS 2.0 Sendai Reprogramming Kit, Publication Number MAN0009378, Revision 1.0), and published protocol of Kyoto University (establishment•maintenance culture of human iPS cells under feeder-free, CiRA_Ff-iPSC_protocol_JP_v140310, http://www.cira.kyoto-u.ac.jp/j/research/protocol.html).

The human iPS cells (DSPC-3 strain) were subjected to feeder-free culturing according to the method described in Scientific Reports, 4, 3594 (2014). As a feeder-free medium, StemFit medium (manufactured by Ajinomoto Co., Inc.) was used, and as a feeder-free scaffold, Laminin 511-E8 (manufactured by Nippi, Inc.) was used.

As a specific maintenance culture operation, the subconfluent human iPS cells were first washed with PBS, and dispersed into single cells by using TrypLE Select (manufactured by Life Technologies). Thereafter, the above human iPS cells dispersed into single cells were seeded in a plastic culture dish coated with Laminin 511-E8, and subjected to feeder-free culturing in Stem Fit medium in the presence of Y27632 (ROCK pathway inhibiting substance, 10 μM). When a 6-well plate (manufactured by Iwaki, for cell culture, culture area 9.4 cm$^2$) was used as the above plastic culture dish, the number of plated cells for the above human iPS cells dispersed into single cells was set to $1.3 \times 10^4$. One day after seeding, the entire amount of the medium was changed with Stem Fit medium free of Y27632. Thereafter, once in 1-2 days, the total amount of the medium was changed with Stem Fit medium free of Y27632. Thereafter, 6 days after seeding, the cells were cultured until subconfluence (60% of culture area is covered with cells).

Figure 10:
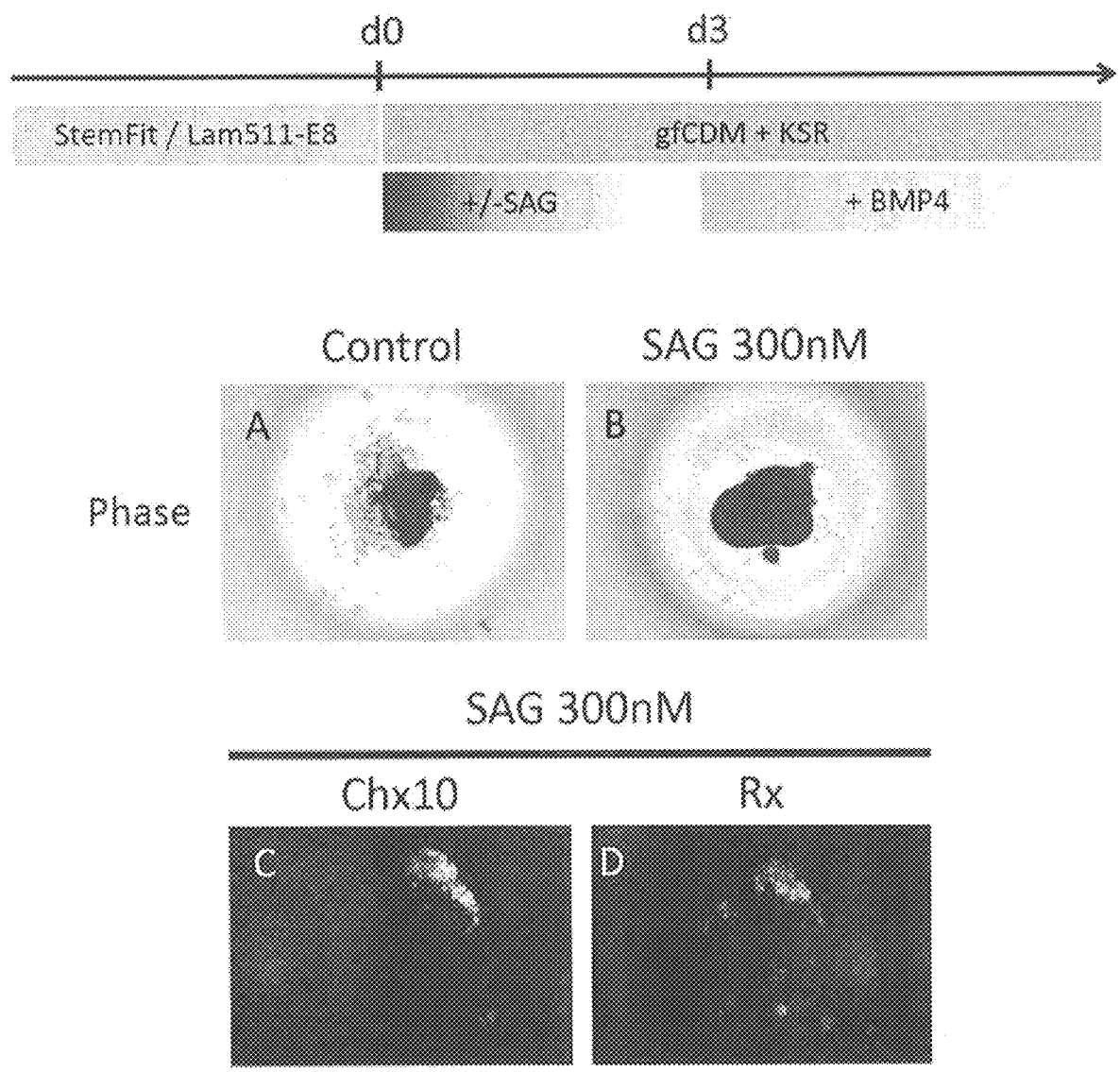
FIG. 10 shows bright field images of aggregates produced is under culture conditions of Example 8 (A, B), and immunostaining images for retinal tissue markers (Chx10, Rx) (C, D).

The thus-prepared subconfluent human iPS cells were treated with the cell dispersion solution by using TrypLE Select (manufactured by Life Technologies), further dispersed into single cells by pipetting operation, and the above human iPS cells dispersed into single cells were suspended in 100 μl of a serum-free medium at $1.2 \times 10^4$ cells per well of a non-cell-adhesive 96-well culture plate (SUMILON SPHEROID V-bottom plate PrimeSurface 96V-bottom plate, SUMITOMO BAKELITE). Thereafter, the cells were subjected to suspension culturing at 37° C., 5% $CO_2$. As the serum-free medium (gfCDM+KSR) therefor, a serum-free medium which is a 1:1 mixture of F-12 medium and IMDM medium supplemented with 10% KSR, 450 μM 1-monothioglycerol, 1× Chemically defined lipid concentrate was used. At the time of the start of suspension culturing (day 0 after the start of suspension culturing, start of step 2), the above serum-free medium supplemented with Y2763 (final concentration 20 μM) and further supplemented with SAG as an exogenous Shh signal transduction pathway activating substance (final concentration 300 nM), or not supplemented with SAG (final concentration 0 nM) was used (FIG. 10). On day 2 after the start of suspension culturing, cell aggregates were formed. On day 3 after the start of suspension culturing, a medium (50 μl) free of Y2763 and SAG, and containing or not containing human recombinant BMP4 was added to adjust the final concentration of exogenous human recombinant BMP4 to 1.5 nM (55 ng/ml) or 0 nM. On day 6 after the start of suspension culturing, a half amount of the medium was changed with a serum-free medium free of Y27632, SAG and BMP4. Thereafter, a half amount of the medium was changed with the above serum-free medium free of Y27632, SAG and BMP4 once per 2-4 days. The thus-prepared cell aggregates were subjected to bright field observation under an inverted microscope (BIOREVO manufactured by KEYENCE) on day 22 after the start of suspension culturing. As a result, it was found that the formation efficiency of the cell aggregates was poor under conditions without addition of a Shh signal transduction pathway activating substance (FIG. 10, Control). On the other hand, it was found that cell aggregates were maintained, and neuroepithelium was formed under conditions with addition of SAG at the start of the suspension culturing (FIG. 10, SAG 300 nM).

Cell aggregates on day 22 after the start of suspension culturing were fixed with 4% para-formaldehyde to produce frozen sections. These frozen sections were immunostained for Chx10 (anti-Chx10 antibody, Exalpha, sheep), which is one of the retinal tissue markers, or Rx (anti-Rx antibody, manufactured by Takara, guinea pig), which is one of the retinal tissue markers. As a result, it was found that, under conditions involving addition of SAG on day 0 of suspension culturing, and addition of BMP4 on day 3 of suspension culturing, the proportion of Rx-positive cells in the total cells was about 10% and the proportion of Chx10-positive cells in the total cells was also about 10% (FIG. 10). Furthermore, from the analysis of the serial sections, it was found that Rx is also strong positive in neural tissues of Chx10-positive cells (FIG. 10). From these results, it could be confirmed that a retinal tissue can also be produced from feeder-free human iPS cells established using Sendaivirus, by adding a Shh signal transduction pathway activating substance at the start of the suspension culturing in step 2 and adding a BMP signal transduction pathway activating substance as a differentiation induction substance during the suspension culturing in step 3.

INDUSTRIAL APPLICABILITY

According to the production method of the present invention, it is possible to induce differentiation of pluripotent stem cells into retinal cells in the absence of feeder cells to produce a retinal tissue. The production method of the present invention is useful since it can produce a retinal tissue to be used as a material for toxicity and efficacy evaluation of pharmaceutical product candidate compounds and other chemical substances, tests for application to transplantation material for a retinal tissue transplantation treatment, or treatments.

The contents disclosed in any publication cited herein, including patents, specifications of patent applications, and scientific documents, are hereby incorporated in their entireties by reference, to the extent that they have been disclosed herein.

This application is based on a patent application No. 2014-217868 filed in Japan (filing date: Oct. 24, 2014), the contents of which are incorporated in full herein.

The invention claimed is:

1. A method for producing a cell aggregate containing a mixture of cells expressing Oct3/4 and cells expressing at least one kind selected from the group consisting of SOX1, N-cadherin, OTX2 and Nestin, comprising the following steps (1) and (2):
   (1) a first step of culturing human pluripotent stem cells in the absence of feeder cells and in a medium comprising a factor for maintaining undifferentiated state of the human pluripotent stem cells, and
   (2) a second step of dispersing the cells obtained in the first step and culturing the dispersed cells in suspension in the presence of a Sonic hedgehog signal transduction pathway activating substance in the absence of a Wnt signal transduction pathway inhibiting substance to form a cell aggregate within about 72 hours after the cells obtained in the first step are dispersed.

2. The production method according to claim 1, wherein the factor for maintaining undifferentiated state is an FGF signal transduction pathway activating substance.

3. The production method according to claim 2, wherein the FGF signal transduction pathway activating substance is bFGF.

4. The production method according to claim 1, wherein, in the second step, the concentration of the Sonic hedgehog signal transduction pathway activating substance in the medium is a concentration corresponding to Sonic hedgehog signal transduction activity of SAG at 10 nM to 700 nM.

5. The production method according to claim 1, wherein the Sonic hedgehog signal transduction pathway activating substance is SAG, Purmorphamine or Shh.

6. The production method according to claim 1, wherein the first step is performed by an adhesion culturing method.

7. The production method according to claim 1, wherein the pluripotent stem cells are induced pluripotent stem cells.

8. The production method according to claim 1, wherein uniform aggregates are formed.

9. The production method according to claim 1, wherein the cell aggregate maintaining an undifferentiated state is formed.

10. The production method according to claim 1, wherein the percentage of cells expressing Oct3/4 is not less than 50% of the total number of cells in the cell aggregates.

11. The production method according to claim 1, wherein, in the second step, the suspension culturing is performed in a serum-free medium.

12. The production method according to claim 1, wherein a period for the culturing in the second step is 12 hr-48 hr.

13. A method for producing a neural cell or neural tissue comprising a step of culturing the cell aggregate obtained in claim 1 in suspension.

14. The method according to claim 13, wherein the culturing in suspension is performed in the absence of BMP signal transduction pathway activating substance.

15. The method according to claim 13, wherein the neural cell and neural tissue comprise a cell expressing Sox2 and/or Pax6.

16. The method according to claim 13, wherein the culturing in suspension is performed using a medium free of a Sonic hedgehog signal transduction pathway activating substance, or wherein the culturing in suspension is performed using a medium comprising a Sonic hedgehog signal transduction pathway activating substance and stepwisely decreasing the concentration of the Sonic hedgehog signal transduction pathway activating substance in the medium.

17. The method according to claim 16, wherein the decreasing of the concentration of the Sonic hedgehog signal transduction pathway activating substance is performed by changing a half amount of the existing medium to a serum-containing medium or serum-free medium free of the Sonic hedgehog signal transduction pathway activating substance.

18. The method according to claim 17, wherein the medium change is performed 1 to 4 times.

* * * * *